United States Patent [19]

Carter

[11] Patent Number: 5,187,506

[45] Date of Patent: Feb. 16, 1993

[54] METHOD AND APPARATUS FOR DETERMINING PHYSIOLOGICAL PARAMETERS BASED ON PUPIL RESPONSE

[75] Inventor: Elbert P. Carter, Wilmington, Del.

[73] Assignee: Fairville Medical Optics Inc., Mendenhall, Pa.

[21] Appl. No.: 589,977

[22] Filed: Sep. 28, 1990

[51] Int. Cl.$^5$ ............................................... A61B 3/10
[52] U.S. Cl. .................................. 351/221; 351/205; 351/223; 351/224
[58] Field of Search ................ 351/205, 221, 223, 224

[56] References Cited

U.S. PATENT DOCUMENTS

| | | |
|---|---|---|
| H574 | 2/1989 | Merkel et al. .................. 351/223 |
| 3,966,310 | 6/1976 | Larson et al. . |
| 4,755,043 | 7/1988 | Carter . |
| 4,815,839 | 3/1989 | Waldorf . |
| 4,850,691 | 7/1989 | Gardner et al. . |

OTHER PUBLICATIONS

W. B. Pickworth et al., "Opiate Induced Pupillary Effects on Humans," *Methods and Findings in Experimental, Clinical Pharmacology*, 1989, vol. 11, pp. 759–763.
A. Radzius et al., "A Portable Pupillometer System for Measuring Pupillary Size and Light Reflex," *Behavior Research Methods, Instruments and Computers*, 1989, 21(6) 611–618.
Jones et al., "A New Solid State Pupillometer Using a Self-Scanning Photodiode Array," *J. Phys. E: Scientific. Instruments*, 16, 12, pp. 1169–1172 (Dec. 1983).
International Application No. PCT/GB90/00648, "Device for Monitoring Body Functions", Glynn et al. (Nov. 1, 1990).

Primary Examiner—Bruce Y. Arnold
Assistant Examiner—Hung Xuan Dang
Attorney, Agent, or Firm—Synnestvedt & Lechner

[57] ABSTRACT

Portable, scanning, self-measuring pupillometers. With pupillometers described herein, cost effective and accurate central nervous system impairment can be quickly determined, thereby reducing worker inefficiency and improving safety. The pupillometers comprise eye orbit housings for positioning at least one eye orbit for scanning by the pupillometer, radiating diodes interfaced with the housings for irradiating at least one eye with scanning radiation, sensing elements adapted to receive reflected radiation from the eye irradiated by the radiating diodes, the sensing elements being further adapted to respond to a contrast between radiation reflected from the iris of the eye and radiation reflected from the pupil of the eye, and centering elements interfaced with the sensing elements for presenting an image of the pupil to a subject on the sensing elements so that the subject can center the image of the pupil on the sensing elements.

23 Claims, 15 Drawing Sheets

STEP 1-1
SET IRED LEVEL TO 10 OR TO USER SELECTED VALUE. IF USING USER-SELECTED IRED VALUE THEN GO TO STEP 2-1.

STEP 1-2
READ THE DIAMETER AND DISCARD TO ALLOW SETTLING AFTER SETTING IRED VALUE. READ THE DIAMETER AGAIN AND SAVE VALUE.

STEP 1-3
IF SAVED DIAMETER IS LESS THAN 10 mm AND GREATER THAN .8 mm THEN GO TO NEXT STEP ELSE GO TO STEP 1-6.

STEP 1-4
IF DIFFERENCE BETWEEN CURRENT DIAMETER READING AND PREVIOUS DIAMETER READING IS LESS THAN 11 PIXELS THEN GO TO NEXT STEP ELSE GO TO STEP 1-6.

STEP 1-5
INCREASE IRED SETTING BY 20% IF DIAMETER IS GREATER THEN 3mm OR BY 10% OTHERWISE. READ DIAMETER. IF THIS READING IS WITHIN 11 PIXELS OF THE READING FROM STEP 1-2 THEN GO TO STEP 1-7 ELSE GO TO NEXT STEP.

STEP 1-6
IF IRED SETTING IS GREATER THEN 200 THEN RESET IT TO 10 ELSE INCREASE SETTING BY 20% IF DIAMETER IS GREATER THAN 3mm OR BY 10% IF DIAMETER IS LESS THAN 3mm GO TO STEP 1-2.

STEP 1-7
CHECK FOR RELEASE OF OPTICAL UNIT SWITCH. IF STILL PRESSED, GO TO STEP 1-2. IF RELEASED, GO TO STEP 2-1.

*Fig. 8A*

STEP 2-8
COMPARE THE ABSOLUTE VALUE OF THE DIFFERENCE BETWEEN THE DIAMETER FROM MOST RECENT STEP 2-3 AND STEP 2-7 TO THE ABSOLUTE VALUE OF THE DIFFERENCE OF THE DIAMETER FROM THE MOST RECENT STEP 2-3. SET THE IRED THE VALUE IN EFFECT FOR THE SMALLEST DIFFERENCE. GO TO STEP 2-10.

STEP 2-9
IF IRED SETTING IS GREATER THAN 200 THEN RESET IT TO 10 AND SET COUNTER. IF COUNTER IS SET INCREASE SETTING BY 10% OR IF COUNTER ISN'T SET INCREASE BY 20% IF DIAMETER IS GREATER THAN 3mm OR BY 10% OTHERWISE. GO TO STEP 2-3

STEP 2-10
IF IRED VALUE IS GREATER THAN 255 THEN SHOW ERROR MESSAGE TO USER AND CANCEL MEASUREMENT.

STEP 2-11
READ DIAMETER AT CURRENT IRED LEVEL. COMPARE TO DIAMETER FROM LAST STEP 2-3. IF DIFFERENCE IS GREATER THAN 6 PIXELS THEN SHOW ERROR MESSAGE TO USER AND CANCEL MEASUREMENT.

*Fig. 8C*

METHOD AND APPARATUS FOR DETERMINING PHYSIOLOGICAL PARAMETERS BASED ON PUPIL RESPONSE

FIELD OF THE INVENTION

This invention relates generally to methods and apparatus for determining pupil size. More specifically, this invention relates to methods and apparatus for determining physiological parameters based on pupil reaction to a light stimulus.

BACKGROUND OF THE INVENTION

In today's complex technical society, government and private workers are frequently asked to perform rigorous and difficult tasks requiring precise motor skills, concentration, and manual dexterity. Workers ranging from trained operators on high speed mass transit lines to research scientists in high technology laboratories must consistently perform with the maximum of their intellectual and motor skills in order to safely and efficiently accomplish their jobs. Unfortunately, today many sensory altering temptations exist which can cause people to temporarily, permanently, or progressively lose the full use of their mental faculties. Narcotics, opiates, depressants, stimulants, alcohol, and both legal and illegal drugs may produce deleterious and destructive effects on an individual's mental and physical performance.

The effects of these substances can be dramatic and oftentimes dangerous to the individual under their influence, and to a public that depends on that individual to be performing adequately. Drug and alcohol abuse have recently been responsible for highly publicized devastating plane and train accidents, and doubtless numerous other smaller catastrophes which have not been reported by the media. Additionally, both government and private industry suffer billions of dollars of yearly losses due to inefficiency, absenteeism, and waste by individuals that are impaired by, or under the influence of, legal and illegal substances which alter their sensory perceptions.

Key segments of society, such as the military, transportation industries, and other private employers are severely burdened with the growing costs that drug and alcohol abuse wreak on worker productivity, and employee and public safety. Conservative estimates report that the annual cost of lost productivity and employment due to drug abuse is 26 billion dollars per year, and for alcohol abuse is 54.7 billion dollars per year. The insurance industry estimates that the cost of injuries, accidents, lost employment and crime due to drug abuse is about 85 billion dollars per year. The United States Chamber of Commerce and the National Institute on Drug Abuse (NIDA) estimate the cost to the national business community due to drug abuse in the workplace may be as much as one hundred billion dollars per year, but when non-business impacts are included in the cost, it may be closer to 200 billion dollars per year.

There has therefore been great emphasis placed by government and private employers in developing and implementing drug control programs, employee assistance programs for drug abuse, and pre-employment drug and alcohol testing. When the high number of sensitive positions are considered in the Departments of Defense, Transportation, Energy, and others, as well as the high number of important positions in private industry, the need for comprehensive, cost-effective, and efficient drug and alcohol impairment testing becomes apparent. All of the aforementioned government and industrial players, are highly concerned by these problems, and have been involved in instituting various kinds of drug and alcohol testing for their employees with an eye towards reducing and eliminating drug and alcohol abuse.

To date, there have been a number of subjective evaluations and objective tests created and implemented which detect alcohol and drug intoxication. The more common definitive objective tests are urine and blood tests (collectively referred to as "body fluid" tests) and, in the case of the impaired motorist, breath tests to determine potential blood alcohol levels and intoxication. Body fluid tests generally require obtaining a sample of an individual's urine or blood and having the urine or blood chemically analyzed to determine the quantitative level of drugs or alcohol in the body. Such body fluid testing has been used for several decades by the police, the military, and corrections officials to identify illegal drug and substance abusers.

Today, the market for sample acquisition and collection for all types of body fluid drug-related testing, processing, and laboratory analysis including report preparation is estimated to be about 750 million dollars per year, with a projected growth rate of about 15-20% through the mid-1990s. However, this projected growth rate will depend on the acceptance of random body fluid testing which is currently under attack by legal challenges related to invasion of privacy, chain of custody issues, and general Fourth Amendment rights. These attacks illustrate a general lack of confidence which both the scientific and legal communities ascribe to body fluid testings. This lack of confidence is a direct result of the inherent unreliability and non-repeatability of body fluid testing in determining impairment.

Furthermore, the cost of body fluid testing is prohibitive for all but the largest companies and governmental agencies. For example, the laboratory analysis costs of an individual two-step urine test that validates positive drug levels with a mass spectrometer is between $35-60. Coupling this cost with the management costs of body fluid testing techniques, which is generally far greater than the analytical test itself because of the need to comply with new government regulations embodied in, for example, 49 C.F.R. §§40, 217, 219, 225, 391, 199; 14 C.F.R. 1, and §121; and 46 C.F.R. §16, the total costs to an employer can range from $200 to $560 per test. Since to be effective body fluid tests must be repeated often, they present a significant financial burden to companies and government agencies that are required to periodically test their workers.

Because body fluid testing exhibits both prohibitive costs and questionable accuracy, efforts have been made to develop other ways to test for drug and alcohol impairment. These efforts generally approach the solution to this problem through the use of non-invasive, non-intrusive methods that utilize electronics and computer equipment to perform the testing. Many types of instruments have been developed for this purpose. One such instrument is the video electronystagmograph disclosed in U.S. Pat. No. 4,815,839, Waldorf.

The Waldorf patent discloses a system for viewing and recording eye movement. See Waldorf, col. 1, lines 7-11. In particular, the Waldorf patent teaches a system which views and records the vertical, horizontal and rotary eye movement of a subject. When a subject is impaired or is suffering from certain diseases, he or she may exhibit "nystagmus" which is a jerky movement of the eyeball. The Waldorf device detects such nystagmus.

However, there has not been clinical confirmation, nor does the Waldorf patent disclose, that nystagmus monitoring is useful in detecting drug or alcohol impairment. No quantitative or qualitative data exists which definitively explains the relationship between nystagmus and various responses to individuals under the influence of opiates, alcohol or other types of drugs. Therefore, the video electronystagmographs disclosed in the Waldorf patent fail to solve a long-felt need in the art for an efficient and accurate apparatus which performs substance impairment testing.

A general class of instruments for measuring pupil diameter and responses have been developed which are called "pupillometers." A pupillometer measures, displays and records pupil diameter before and after a light stimulus causes a constriction and redilation of the pupil. Early results published in W. B. Pickworth et al., "Opiate Induced Pupillary Effects on Humans, "*Methods and Findings in Experimental, Clinical Pharmacology*, 1989, Vol. 11, pgs. 759-763, indicate that opiates cause systematic changes in the dynamic pupillary responses in humans and that measurement of these changes may be useful in a quantitative estimate of drug-induced impairment. Furthermore, it has been determined that opiates cause dose-related decreases in pupil size and decreases in the velocity of constriction and dilation of the pupil following a light stimulus. NIDA has thus determined that pupillometers in drug abuse treatment settings and basic research laboratories will offer efficient methods of assessing exposure to psychoactive drugs. See A. Radzius et al., "A Portable Pupillometer System for Measuring Pupillary Size and Light Reflex," *Behavior Research Methods, Instruments and Computers*, 1989, 21(6) 611-618.

At the present time, laboratory pupillometers have been developed to study pupil size and reactivity as indicators of central nervous system activity directly related to the body's reaction to external stimuli such as light, and internal stimuli such as drugs, alcohol, fatigue, anxiety, and psychopathic states. Additionally, pupillometry has been used over the past twenty years in clinical research for diagnosing various symptoms in anesthesiology, diabetology, trauma assessment and, most recently, in measuring psycoaddictive drug effects and other substance abuses. However, advances in pupillometry have been hampered because technicians and medical personnel have had to depend strictly upon bulky, difficult to use, and unreliable instruments that require a high level of operating skill. Many types of prior pupillometers have also been extremely costly.

Other kinds of pupil diameter measuring instruments have been developed which use high speed close-up cameras, video cameras, and infrared pupillometers. Prior infrared pupillometers offering automatic data reduction and analysis are bulky, cumbersome, unreliable, and cost between $30,000 and $150,000 for a single instrument. These instruments also generally have limited automatic data analysis features and may require cumbersome analysis of data which is time consuming and inefficient.

However, the advantages of pupillometers outweigh the advantages of body fluid tests which have heretofore been used to indicate drug or alcohol impairment. Pupillometers provide immediate, real time, and direct indication of impairment due to neurological compromise which has been shown to cause altered pupil size, and degraded pupil response to external stimulus. Thus, pupil response indicates impairment due to medications and illegal drugs. Additionally, pupillometer readings can be done in a low cost, repetitive environment and exhibit from tens to hundreds of times the reduction in cost compared to the costs of body fluid tests. Such advantages have not been fully realized, since there has yet to be developed an efficient and accurate pupillometer to perform alcohol or drug impairment testing because of the aforementioned problems that exist with prior pupillometers.

An example of a prior pupillometer can be found in U.S. Pat. No. 4,850,691, Gardner et al. The Gardner et al. patent discloses a method and apparatus for determining pupillary response with minimum effects from artifacts. See Gardner et al., col. 5, lines 1-27. The Gardner et al. patent further teaches a pupillometer comprising a means for establishing a dark field condition around the eye, and means within the dark field for irradiating the eye before pupil measurements are made. Measurements with pupillometers disclosed in the Gardner et al. patent require the storing of a quiescent level of radiation and irradiating the eye with a pulse of visible light to make comparisons of the reflections of the visible light with the quiescent radiation before the pupil size can be determined. These functions are accomplished by a number of electronic amplifiers and storage devices adapted to perform data manipulation and control. Furthermore, independent electronic instrumentation is required to perform the pupil measurements discussed in the Gardner patent. See Gardner, col. 7, lines 28-63.

The Gardner et al. patent discloses a complex and cumbersome machine which requires the use of a significant amount of costly computer hardware and instrumentation before pupil measurements are obtained. Furthermore, the device taught in the Gardner et al. patent makes pupil size measurements as a function of time in the form of a difference signal which is inaccurate and encourages the detection of artifacts, which is highly undesirable. The pupillometer disclosed in Gardner et al. cannot adequately eliminate errors produced by artifacts since the pupillary light response monitor taught therein is strongly affected by ambient light which has not been removed with the goggles that cover the subject's eyes. Thus the pupillometer disclosed in the Gardner et al. patent does not satisfy a long-felt need in the art for a pupillometer which efficiently performs pupil size measurement. Furthermore, the Gardner et al. pupillometer cannot perform adequate drug impairment testing because of the aforementioned infirmities apparent from its construction.

Other pupillometers have been developed and are disclosed in, for example, U.S. Pat. No. 4,755,043, Carter. The Carter patent discloses a portable, automatic scanning pupillometer for inspecting holes and gaps, for example a pupil, of up to about 10 millimeters in diameter. See Carter, col. 1, lines 51-66. The Carter patent further teaches a pupillometer which comprises a hand-held optical unit for measuring and stimulating the pupil, and supporting electronics mounted on a main processor circuit board wherein operating software is stored on an EPROM chip. An external computer may be used to control the hand-held device. Furthermore, the Carter patent teaches that an operator of the pupillometer, usually a technician trained to test a subject, must focus a reticle marked with concentric circles through an eyepiece to center the pupil image so that pupil scanning can occur.

While the hand-held pupillometer disclosed in the Carter patent provides an excellent optical system for measuring pupil response, it fails to provide efficient pupillometry which can be used for drug and alcohol impairment testing because it does not stabilize the subject's head, does not provide a focussing point for the subject to stabilize the eyes, and does not provide a stable measuring platform. The Carter pupillometer thus requires extensive practice by an independent technician to achieve efficient use and is not a self-measurement device. Rather, the pupillometer disclosed in the Carter patent must be aligned by the technician, rather than the subject. However if a technician is not adequately trained in the use of the devices, or the subject is uncooperative or under any influence of drug or alcohol, the complicated alignment protocol required by the Carter pupillometer will not allow for efficient and time-effective pupillometric measurements. Furthermore, the Carter patent does not disclose or teach an alignment system with appropriate software enhancements to provide ease of operation, especially for non-technical users.

There therefore exists a long-felt need in the art for self-measuring, portable electronic pupillometers which may be used for efficient and economical determinations of drug or alcohol impairment. This need has not been solved by any of the prior devices discussed above. The novel features, operation and advantages of methods and apparatus provided in accordance with the present invention will be better understood in light of the aforementioned problems, and further in view of the detailed description of preferred embodiments read in conjunction with the accompanying drawings.

SUMMARY OF THE INVENTION

Self-measuring pupillometers provided in accordance with the present invention solve the aforementioned problems associated with prior pupil monitoring devices and fulfill a long-felt need in the art for cost-effective, efficient, and easy to use devices for determining whether a subject is central nervous system impaired. By using pupillometers described and claimed herein, private employers and government agencies will be able to ensure that their workers are performing to the utmost of their intellectual abilities and that these workers can withstand the mental and physical rigors associated with their particular job tasks. Since the pupillometers herein disclosed provide real-time assessment of central nervous impairment, virtually all dangerous and life threatening situations that come about as a result of drug and alcohol abuse will be eliminated. Thus, the public will be greatly benefitted because it will be safe from catastrophes caused by workers that cannot perform adequately due to impairment.

In accordance with the present invention, portable scanning, self-measuring pupillometers provide these advantageous results. Preferably, the pupillometers comprise eye orbit housing means for positioning at least one eye orbit for scanning by the pupillometer, radiating means interfaced with the housing means for irradiating at least one eye with scanning radiation, sensing means adapted to receive reflected radiation from the eye irradiated by the radiating means, the sensing means being further adapted to respond to a contrast between radiation reflected from the iris of the eye and radiation reflected from the pupil of the eye, and centering means interfaced with the sensing means for presenting an image of the pupil to a subject on the sensing means so that the subject can center the image of the pupil on the sensing means.

Methods provided in accordance with the present invention also satisfy the long-felt needs discussed previously. Pupillometers provided in accordance with the present invention are significantly more reliable than body fluid tests and have the added advantage of accurate repeatability, thereby greatly reducing the possibilities for error associated with body fluid tests. Furthermore, the pupillometers taught herein give accurate pupil measurements at a fraction of the cost of body fluid tests.

Further in accordance with the present invention, methods of determining whether a subject is central nervous system impaired exhibit all of these desired results. Preferably, the methods comprise the steps of allowing a subject to center at least one pupil on a sensing element in a self-measuring pupillometer, setting a level of scanning radiation to provide substantially optimal indications of the apparent diameter of an image of the pupil on the sensing element, monitoring the pupil's responses to a light stimulus to determine a pupil parameter indicative of impairment and gathering data relating to the pupil parameter, processing the data relating to the pupil parameter to obtain reduced pupil data, and determining a level of central nervous system impairment from the reduced pupil data.

BRIEF DESCRIPTION OF THE DRAWINGS

FIGS. 8A-8C are a flow chart of a preferred method for setting the optimal illumination level of the scanning infrared radiation.

DETAILED DESCRIPTION OF PREFERRED EMBODIMENTS

Figure 1:
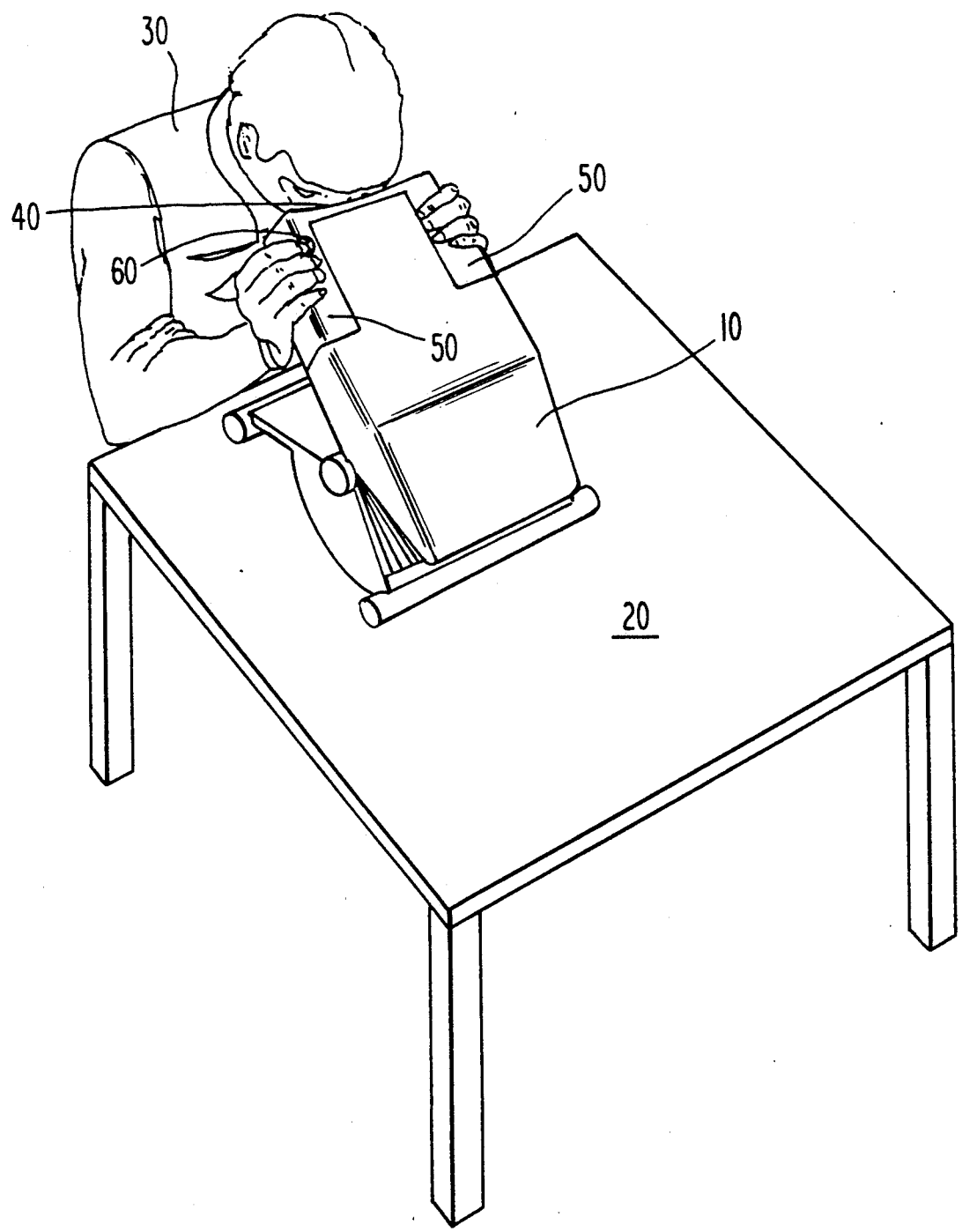
FIG. 1 is an isometric view of a subject being tested with a pupillometer provided in accordance with the present invention wherein the pupillometer rests on a table as shown.

Referring now to the drawings wherein like reference numerals refer to like elements, in FIG. 1 a pupillometer in accordance with the present invention is shown at 10. One of the numerous advantageous aspects of pupillometer 10 is that it can be adapted to sit on a laboratory or clinical table 20 in a stationary position. By placing pupillometer 10 on table 20 for pupillometric measurements, the subject under test 30 can steady the pupillometer and himself so that the measurements can be performed efficiently and quickly.

In preferred embodiments, subject 30 places his or her eye orbits against an eye orbit housing means 40 for scanning. The subject then preferably grasps a pair of hand grips 50 and actuates the pupil scanning process with an external switch 60 that triggers the pupillometer's scanning action.

Figure 2:
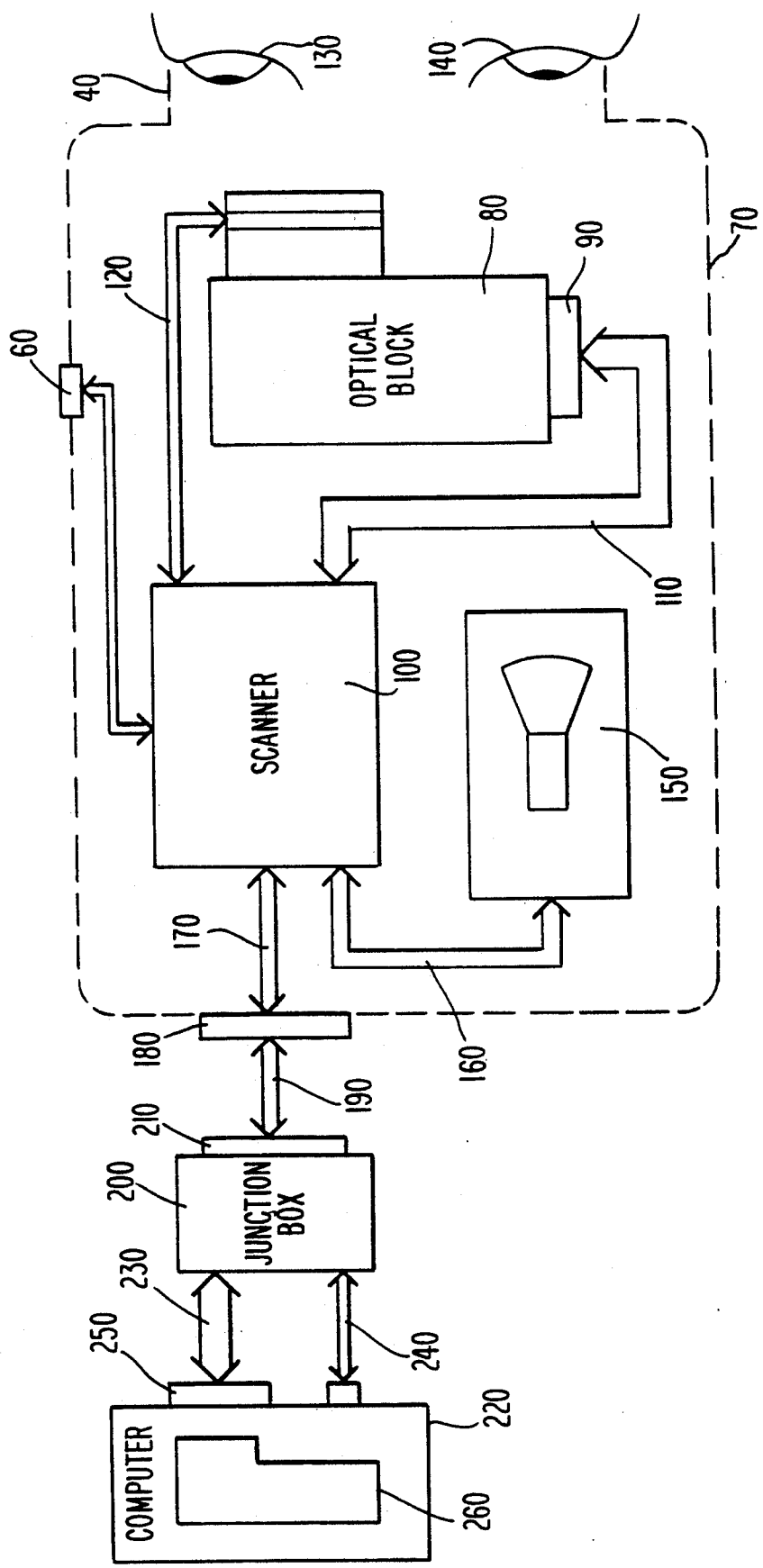
FIG. 2 is a block diagram of a preferred embodiment of a pupillometer provided in accordance with the present invention.

Referring now to FIG. 2 a block diagram of a preferred embodiment of pupillometer 10 is illustrated, along with computer support equipment which may be utilized in pupil scanning techniques provided in accordance with the present invention. In preferred embodiments, pupillometer 10 comprises a housing 70 which supports the pupillometer structure and internal hardware. In further preferred embodiments, pupillometer 10 comprises optical block means 80 that comprises a sensing element 90 which may be, for example, an image sensor such as a charged coupled device (CCD), spatial light modulator (SLM), or more preferably a dynamic random access memory (RAM) chip which is partitioned into pixels that are adapted to detect differences in radiation reflected from relative light and dark areas in the eye. Even more preferably, the dynamic RAM chip is an IS32 OpticRAM manufactured by Micron Technology, Inc., of Boise, Idaho. OpticRAM 90 comprises 65,536 individual radiation sensing elements or "pixels" which are organized into two rectangles of 128×256 pixels each. The OpticRAM may also be used as a 256×256 array of pixels which can indicate relative light or dark.

In further preferred embodiments, scanning means 100 is interfaced to optical block 80 through sensing element 90 by a pair of ribbon cables 110 and 120. Scanning means 100 may be, for example, a printed circuit board (PCB) which comprises the various integrated circuits and logic devices that electronically perform the pupillometric scanning functions for pupillometer 10. Switch 60 is further interfaced to scanning means 100 so that when a subject actuates the pupillometer, scanning means 100 outputs signals through cables 110 and 120 to optical block 80 to begin pupil scanning.

Scanning will occur when the subject places its eyes 130 and 140, against the eye orbit housing means 40 which preferably is mounted to housing 70 and provides assistance in positioning the eye orbits relative to the optical axis of the pupillometer. In preferred embodiments, optical block 80 only scans one pupil, for example, the pupil in eye 130, while eye 140 is simply masked by eye orbit housing means 40 from the optical block. The subject disregards the blank field of view of the unmeasured eye, and pupillometry is performed only on the single eye 130. However, it will be understood by those with skill in the art that certain applications of pupillometry provided in accordance with the present invention may call for scanning of both eyes to compare and measure the pupil dilation and constriction velocities of both eyes. The present invention is equally suited for single pupil measurements or dual pupil measurements.

In accordance with the present invention, centering means 150 is interfaced through cable 160 to scanning means 100 and is aligned with the optical axis of optical block 80. In operation of the pupillometer provided in accordance with the present invention, optical block 80 projects an image of the subject's eye 130 onto the OpticRAM 90. One of the functions of scanning means 100 is to output a signal indicative of the position of the pupil image on the OpticRAM 90 to centering means 150. In preferred embodiments, centering means 150 provides an image of the pupil which is viewable by the subject through the eye orbit housing means 40 and optical block 80 and shows the pupil's position on the OpticRAM 90 to the subject. In this fashion, the subject can adjust the position of its eyes in the eye orbit housing means 40 and self-center the pupil image on the OpticRAM so that accurate pupil scanning can occur.

Centering means 150 thus provides a fast and efficient method for centering the subject's pupil on the pupillometer to perform measurements. By implementing centering means 150, the pupillometer 10 becomes a "self-measuring" device which allows pupillometry to be performed entirely by the subject under test. Thus, the need for a separate pupillometry technician is eliminated, thereby greatly reducing the cost of performing pupillometric measurements, or drug and alcohol impairment testing. Pupillometers provided in accordance with the present invention exhibit a great advantage over prior pupillometers which require independent technicians to make measurements.

Centering means 150 is, for example, a video monitor which displays the pupil position on OpticRAM 90. In further alternative embodiments, centering means 150 is a separate cathode ray tube (CRT) or other type of monitor independent of scanning means 100 which independently provides the pupil's image on OpticRAM 90 to the subject. Other preferred embodiments of centering means 150 and equivalents thereof which allow pupillometers to become self-measuring instruments as described above will be apparent to those with skill in the art, and all are intended to be within the scope of the present invention.

In yet further preferred embodiments of systems provided in accordance with the present invention, scanning means 100 is interfaced through cable 170 and connector 180 to yet another ribbon cable 190, preferably a number twenty-eight AWG ribbon, and to a junction interface means 200. In still further preferred embodiments, junction interface means 200 comprises a connector 210 adapted to connect the ribbon cables previously mentioned.

Junction interface means 200 preferably provides an interface from pupillometer 10 to an outside environment. In preferred embodiments, junction interface means 200 is interfaced to processing means 220 through yet another set of cables 230 and 240. The processing means may be, for example, a personal computer (IBM XT or AT compatible with MS DOS) and in more preferred embodiments, is a COMPAQ Portable III computer. In the case of the COMPAQ Portable III computer, cable 230 is a 15-wire ribbon cable which interfaces 250 to the computer 220. Cable 240 is a power cable which provides 12 volts at 1.6 amps to the junction interface means 200 and ultimately to pupillometer 10. Ribbon cable 230 is connected at 250 to a computer interface board 260 which is a PCB that interfaces computer 220 to function with pupillometer 10.

Computer 220 provides data processing functions and lo control for the pupillometer 10, and more particularly to scanning means 100. Interface PCB 260 preferably comprises the integrated circuits and logic devices needed to control the various functions provided by pupillometer 10. Furthermore, interface PCB 260 allows the central processing unit (CPU) in computer 220 to receive and process information according to the particular protocols and programs established by the operating system in computer 220.

Computer 220 and junction interface means 200 could be integrated in a self-contained pupillometer unit, thereby eliminating the need for separate portable computers and their attendant cable connections 190, 240 and 230. Such a system could also be made portable and placed on a table while maintaining all of the advantages of pupillometers heretofore described. With the separate computer arrangement described above however, computer 220 could be located at a different location from pupillometer 10 so as not to disturb the subject performing self-measuring tests, or to support a number of pupillometers simultaneously. All such arrangements are encompassed within the scope of the present invention.

Figures 3A, 3B:
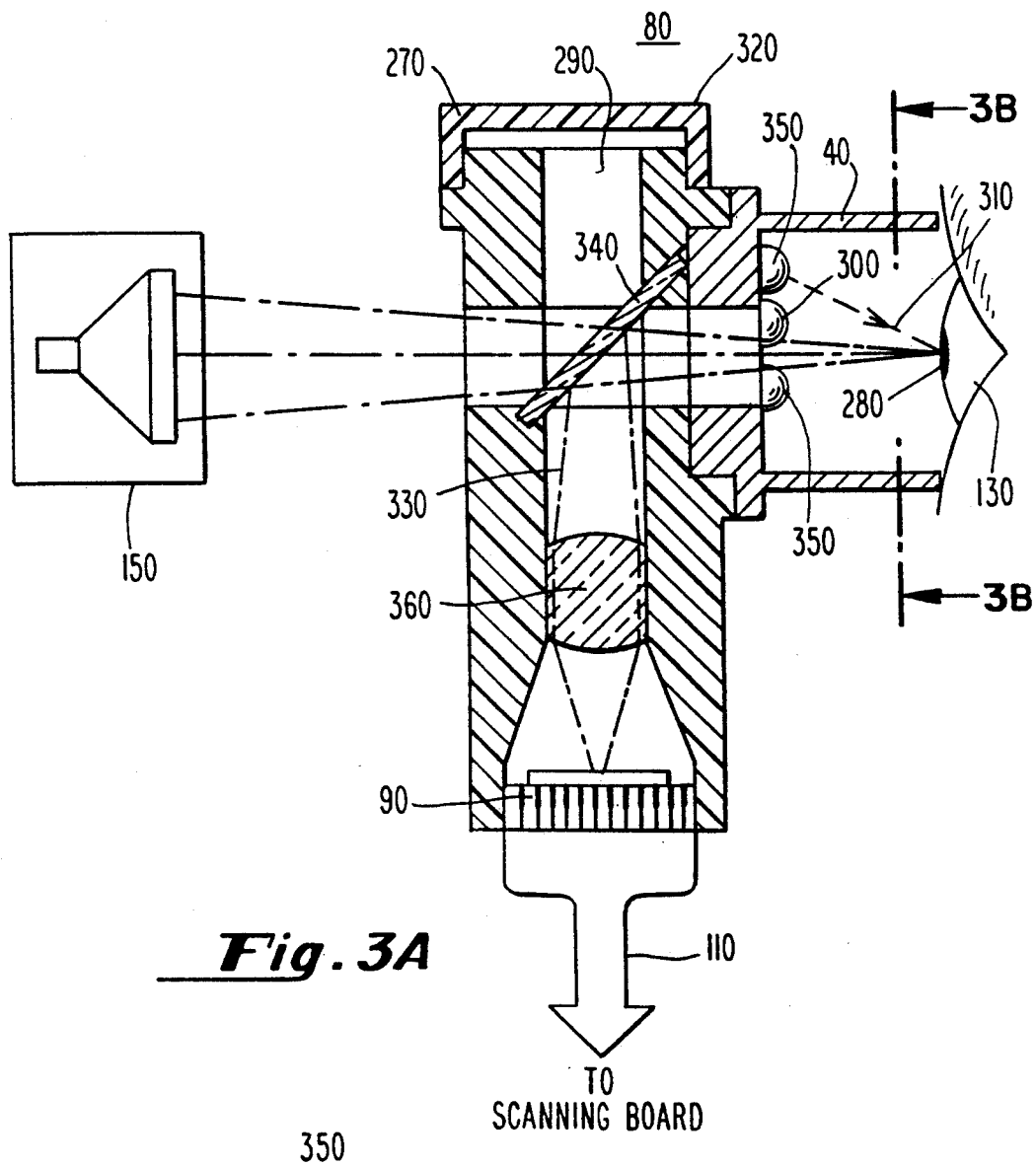
FIG. 3A is a schematic view of an optical block in pupillometers provided in accordance with the present invention for irradiating the pupil with visible and scanning radiation.
FIG. 3B is a view of an IRED ring provided in accordance with the present invention.

Referring to FIG. 3A, optical block 80 comprises a housing 270 which houses the optical and electronic components that will measure the size of pupil 280 in eye 130 The subject views the image of the eye as it appears on the centering means 150 so that the subject can center the pupil image on OpticRAM 90. OpticRAM 90 is preferably housed in a main tube 290 of optical block 80 substantially perpendicular to the line of sight of monitor 150.

During the scanning process, each of the 65,536 pixels on the OpticRAM is biased according to a power supply voltage of 5 volts DC and further according to a characteristic capacitance in each OpticRAM pixel. If the voltage on a particular pixel capacitance is discharged below a presettable level, that pixel will read out as light on the next scan. Otherwise, the pixel will indicate dark. The contrast difference between the iris and the pupil is adequate for the light-dark discrimination between the iris and the pupil edge. In preferred embodiments, a complete scan can be accomplished every tenth of a second. However, scans may be accomplished every twentieth of a second or at higher rates, depending upon the desired resolution for the pupillometer and in the particular applications for which the pupillometer will be used.

The IS32 OpticRAM 90 is a geometric arrangement of 256 rows and 256 columns of pixels with rows stretched to 512 element positions. Scanning means 100 preferably scans the 256 column positions for each row in the sequence and data bits are transmitted serially to PCB 260 at a three MHz rate. In preferred embodiments, the 256 column positions for each row sequence are assembled into 8-bit bytes and stored in an 8K by 8-bit static RAM (SRAM) chip. A full scan takes about 22 milliseconds, and a new scan is started 78 milliseconds later. Ideally, the image of the pupil for each row is merely a continuous string of dark bits. A row with the most dark bits corresponds to the desired diameter. However, since there is noise in the signal corresponding to the pupil's diameter, data bits for several adjacent rows are examined and the most probable pixel count is selected. The diameter is then calculated using known optical reduction ratios and pixel spacings.

Pupillometric measurements are made when the subject puts his or her eyes in the eye orbit housing means 40 and activates the scanning process with switch 60, or a technician activates the process with a remote switch. The subject then focuses and centers the iris and pupil image as seen through the centering means 150, which in preferred embodiments is a CRT monitor. Alternatively, an operator can coach the subject to move his or her eye to center the image as the operator refers to the pupil image which can be displayed on the computer monitor visible to the operator. The scanning means 100 begins scanning when the subject presses switch 60. When the switch is released, infrared illumination is adjusted to an optimum level and initial pupil diameters are acquired and stored according to the particular protocol programmed into computer 220.

When the initial pupil diameter is obtained, stimulus means 300 emits a visible light pulse of programmable duration and intensity. The visible light pulse causes the pupil to constrict and when the visible light pulse diminishes, the pupil dilates. Scanning radiation which does not cause pupil response or reaction simultaneously illuminates the eye and is reflected from the iris and the pupil of the eye to the OpticRAM. Preferably, the stimulus means 300 is an array of light-emitting diodes. Even more preferably, the array of light-emitting diodes comprises two light-emitting diodes which radiate a green pulse of visible light. Stimulus diodes 300 irradiate the eye for about 0.2 to about 1.0 seconds but may be left on for the entire pupil contraction and redilation time depending on the particular application.

In preferred embodiments, pupil reaction is obtained every tenth of a second, but may be obtained every twentieth of a second when faster scan times are required. In further preferred embodiments, data from each scan is accumulated between from about one to about seven seconds from the start of the visible light pulsing from stimulus diodes 300. Light 310 from stimulus diodes 300 impinges eyes 130 causing pupil constriction. In still further preferred embodiments, a set of irradiating diodes, shown generally at 350, provide scanning radiation to be reflected from the pupil and iris so that a contrast difference between the pupil and iris can be obtained. The scanning radiation reflects 320 from the pupil and iris and is directed 330 to OpticRAM 90 by a beam splitter 340. In yet further preferred embodiments of pupillometers provided in accordance with the present invention, the irradiating diodes 350 are infrared emitting diodes (IREDs) which supply infrared radiation for scanning and reflection from the pupil. The infrared radiation preferably has a narrow bandwidth peaking at about nine hundred and forty nanometers.

When the IREDs 350 irradiate the pupil and iris, infrared radiation is reflected back from the pupil and iris through beam splitter 340 and is focused by a focusing lens 360 onto the OpticRAM 90. Signals from OpticRAM 90 are then bussed at 110 to the scanning means 100 for pre-processing and ultimately to the computer for processing of the pupil's constriction and dilation velocities, thereby indicating whether the subject is impaired. The IREDs 350 are generally oriented in preferred directions in order to obtain substantially optimal scanning measurements. Optical scanning with similar electro-optic hardware is taught in U.S. Pat. 4,755,043, Carter, at column 4, lines 55 through column 5, line 20, the teachings of which are specifically incorporated herein by reference.

Referring to FIG. 3B, the arrangement of IREDs 350 and stimulus diodes 300 in an "IRED ring" formed around eye orbit housing means 40 as shown. Four IREDs 350 ring the outside of a circle and provide scanning radiation to the eye 130. The green stimulus diodes 300 fall at the center of the ring and provide stimulating radiation which causes pupil constriction. The IRED ring is interfaced 120 with the scanning board to provide data to the scanning board for control of the scanning radiation from the IREDs and the stimulus radiation from the green diodes 300.

Figure 4:
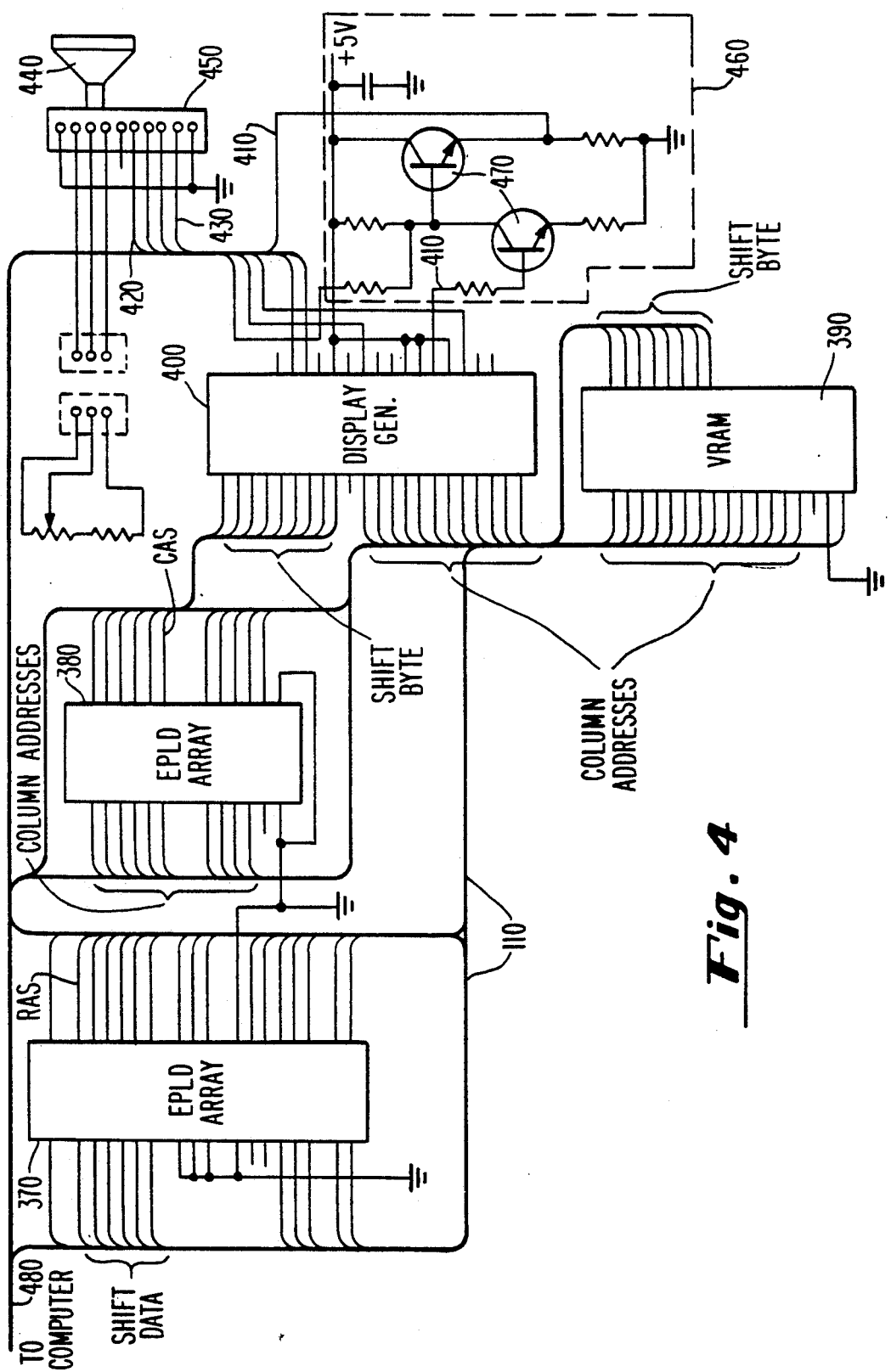
FIG. 4 illustrates a schematic layout of a printed circuit board adapted to control scanning of a pupil to obtain pupil parameters.

The 64K OpticRAM outputs a signal through cable 110 to the scanning PCB 100, a preferred embodiment of which is shown in FIG. 4. The signal on cable 110 is a serial bit stream output from OpticRAM 90. In preferred embodiments, a pair of electronic programmable logic devices (EPLDs) 370 and 380 are adapted to provide the address and control sequences for scanning the OpticRAM and to process the signal returned from the OpticRAM. In further preferred embodiments, EPLD 370 is an EPM 5064 logic array, and EPLD 380 is an EPM 5032 logic array.

EPLD 370 generates the address data as well as row address strobe (RAS) and column address strobe (CAS) signals for the OpticRAM. The EPLD 370 preferably also outputs a "data in" signal to reset each pixel after it has been read. A "data out" signal is also received by EPLD 370 and assembled into 8-bit words. EPLD 370 programs the string of these words or bytes in a video random access memory (VRAM) chip 390 with help from EPLD 380.

EPLDs 370 and 380 are also adapted to perform direct memory addressing (DMA) for the pupillometer CRT monitor circuitry provided in accordance with the present invention. Thus in preferred embodiments, EPLD 370 performs "shift register" functions and other functions which allow the scanning PCB to load the VRAM chip with pixel value data from OpticRAM 90.

EPLD 380 is further adapted to generate address values for the columns of data in OpticRAM 90 so that pixel value data can be loaded onto the correct locations in the VRAM. EPLD 380 also buffers the horizontal and vertical sync (HS and VS, respectively) signals, monitor frame data, and boundary data which are used by the monitor as it displays graphical data corresponding to the pupil and iris position on the OpticRAM. Additionally, EPLDs 370 and 380 provide timing pulses which direct loading of the VRAM with data from the OpticRAM.

In further preferred embodiments of the scanning PCB provided in accordance with the present invention, VRAM chip 390 is interfaced with EPLDs 370 and 380. VRAM 390 is preferably an 8K byte by 8-bit static RAM which is used to store the pupil's image data from OpticRAM 90 according to pixel values and addresses generated by EPLD 380. The data from each row of pixels is stored in 32 consecutive 8-bit bytes in VRAM 390. In this fashion, VRAM 390 acts as a frame buffer for holding data according to pixel values which are ultimately displayed on the monitor 150 so that the centering functions provided in accordance with the present invention can be accomplished.

The scanning PCB also comprises a video display generator (VDG) chip shown at 400. In preferred embodiments, VDG 400 is an MC 6847 video display generator which raster scans VRAM 390 to generate video signals that are then output to monitor 150 so that centering of the pupil on the OpticRAM can be accomplished. VDG 400 is preferably adapted to read the column addresses from VRAM 390 as sequenced from EPLD 380, and translates the fixed data from each block of 32 words into the data from one horizontal sweep of the cathode ray tube (CRT) 440. In still further preferred embodiments, VDG 400 outputs video data 410, as well as HS signal 420 and VS signal 430 to the cathode ray tube 440 in monitor 150 which is interfaced to the scanning PCB through a connector shown generally at 450.

Video signal 410 is preferably boosted by a driving circuit, shown generally at 460, that comprises a pair of 2N222 transistors 470 which provide the desired amplification of video signal 410 that originates at the video output pin of VDG 400 and which carries the pupil pixel information input to VDG 400 from VRAM 390. Video signal 410, HS signal 420, and VS signal 430, as well as the 12-volt power, are output to the monitor 440 through the connector 450. In this manner, a graphical depiction of the pupil and iris can then be displayed on CRT 440 in monitor 150 so that the centering function provided in accordance with the present invention can be accomplished by the subject.

Control for the scanning PCB is provided by the board-modified computer described previously. Data from the scanning PCB is therefore bussed 480 to the computer. In order for the computer to provide control to the pupillometer and for data processing to occur, interface PCB 260 comprising interface electronics is provided to computer 220 so that signals from the pupillometer containing pupil parameters and other data can be processed by the computer's CPU.

Referring to FIGS. 5A–5E, an interface PCB comprising interface electronics for the pupillometer and computer is shown. The main connector to the scanning board is shown generally at 490 ("J1" in FIG. 5C). Preferably connector 490 is a standard ribbon cable adapted to carry parallel signals to and from the pupillometer. The interface PCB communicates with the computer through the card edge connector 520 ("P1" in FIG. 5E) so that the computer can program and control the pupillometer operation. Data from the pupillometer is assembled and stored in a SRAM U7 (FIG. 5A) from which the data can be accessed by the computer through the connector 520 for analysis. In further preferred embodiments, an interface board could be configured to deliver the pupillometer data through connector 520 directly to the computer for assembly, storage and analysis, thereby requiring faster processing equipment. In still further preferred embodiments, SRAM U7 is an HM6264 chip which is an 8-bit, 64K device.

The pixel data stream from the OpticRAM and two timing signals are preferably bussed from the scanning board of the pupillometer to the interface PCB. The bus 510 conducts the timing signals to the buffer chip U1 (FIG. 5B) from which they are applied to a shift register U9 and address counters U10 and U11. Preferably, shift register U9 assembles the pixel data into 8-bit bytes for storage in the SRAM U7. In preferred embodiments buffer chip U1 is a 74LS541 8-bit input/output (I/O) buffer, shift register U9 is a 74LS595 shift register with an 8-bit output, and counters U10 and U11 are 74LS590 integrated circuit chips. One of the timing signals triggers one of two dual monostable multivibrators U2 which in turn triggers the other monostable to provide a sequence of two delayed pulses which are directed to U9, U10, U11 and U7 to store the data bytes. Preferably, monostables U2 are 74LS221 monostable multivibrators. The first multivibrator pulse also disables the address buffer chips U3 and U5 (74LS541 8-bit I/O address buffers) and the data buffer chip U12 (a 74LS541 buffer) through which the computer accesses the pixel data in the SRAM U7 for analysis. Selection of the particular address location which the computer will find the SRAM U7 is made by the programmable array logic (PAL) U6 along with the six position jumper plug P2. Preferably PAL U6 is a PAL 16L2 chip. Any one of six 8K blocks of computer memory can be selected to position the SRAM address at an otherwise unused location.

Programming and control of the operation of the pupillometer is accomplished through the programmable parallel I/O and timer chips Z7 and Z8. Preferably chips Z7 and Z8 are 8255 timer chips. The Z7 PI/O unit provides three 8-bit ports, PA, PB and PC. The PB port drives an 8-bit digital to analog converter (DAC) Z10 (preferably an AD558 DAC chip) to generate an analog signal level for the IRED current controller/driver consisting of the operational amplifier Z12 (a CA3140 chip) and power transistor 540 which preferably is an MPSU45 bipolar NPN transistor. Three bits of the PA port select the stimulus diode current provided by a transistor driver 570. The PC port is preferably divided into two 4-bit sections. The lower 4-bit nibble is programmed for output while the upper 4-bit nibble is preferably set for input. Furthermore the timing chip Z8 comprises three programmable 16-bit counters. The 16-bit counters are preferably preset under computer control and when counted down to zero, issue pulses, reset themselves, and repeat issuing pulses until the computer stops them. Chip Z6 is a crystal controlled computer-type clock oscillator, typically running at about 2MHz. The oscillator drives the first counter of the Z8 programmable counter which is preset to count out and deliver a pulse about every one millisecond. This 1KHz pulse stream drives the other two counters, one of which preferably provides timing of the ten (or alternatively twenty) frames per second for the pupillometer, while the other is preset for the frame scan time and tells the computer when to start the analysis of the frame. Signals to and from the Z8 timer pass through the PC port of the PI/O chip Z7. This port also preferably inputs the signal from the pupillometer's switch 60.

The PAL Z4, along with the four position jumper block P3, selects the I/O addresses at which the computer will find the Z7 and Z8 units for input/output. Any one of four I/O address blocks can be selected with the jumper plug at installation. In preferred embodiments, the I/O data is channelled through the bi-directional bus buffer Z1 under the control of the PAL Z4. In still further preferred embodiments, PAL Z4 is a PAL 14L4 integrated circuit chip.

Figure 5A:
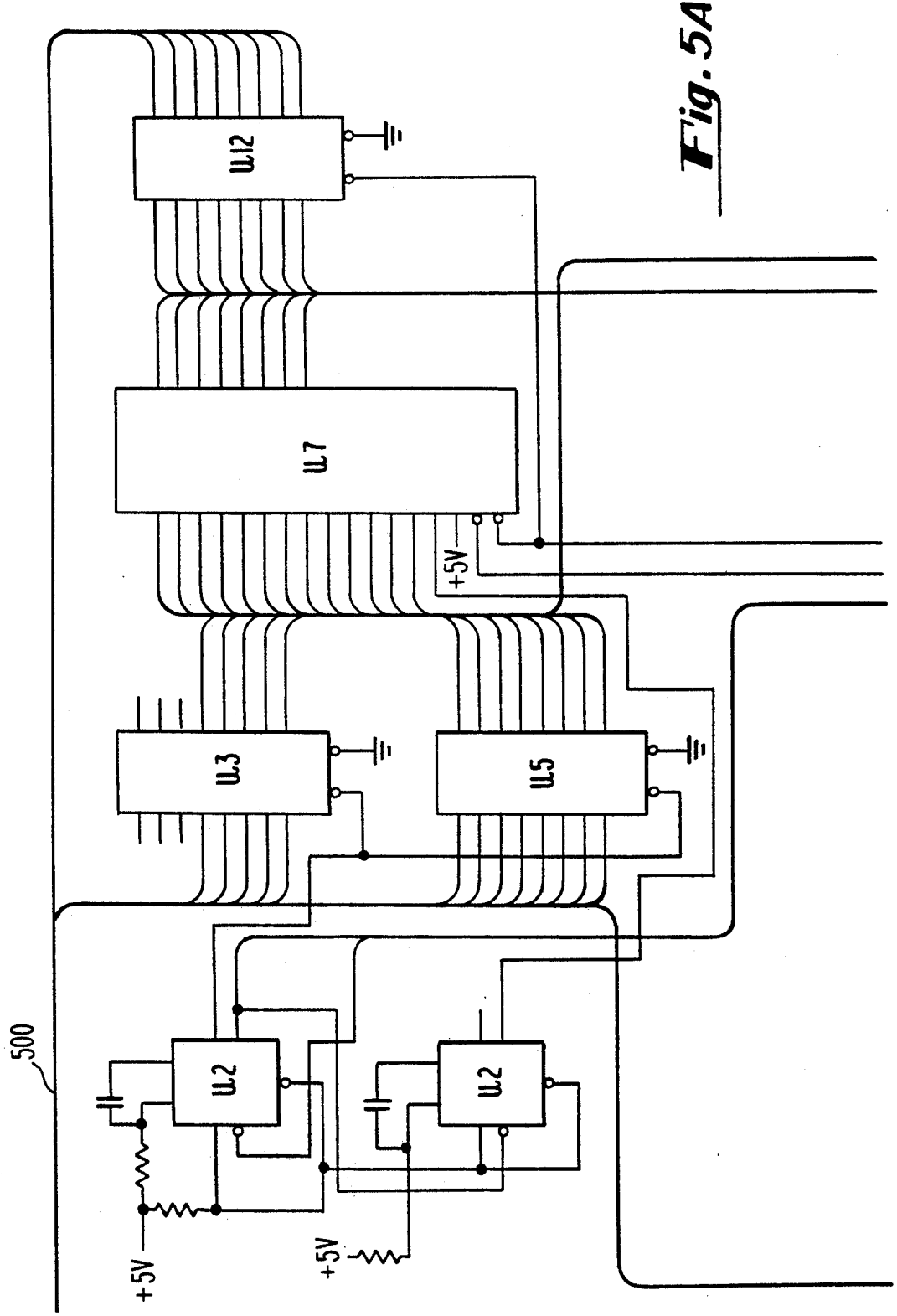
FIGS. 5A-5E are a schematic layout of a printed circuit board adapted to interface pupil parameter data to a computer so that the pupil parameter data can be reduced and processed.
Figure 5B:
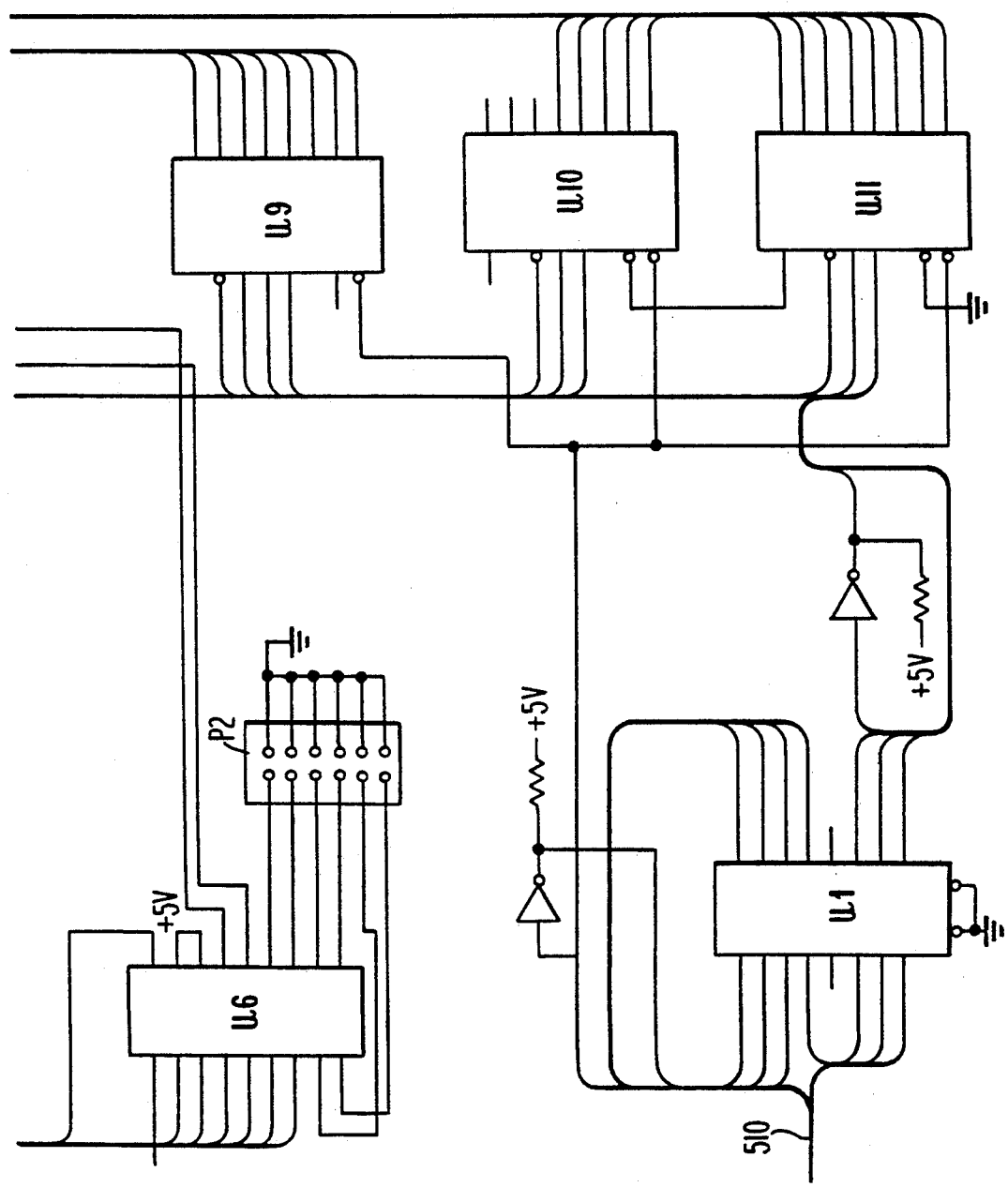
Figure 5C:
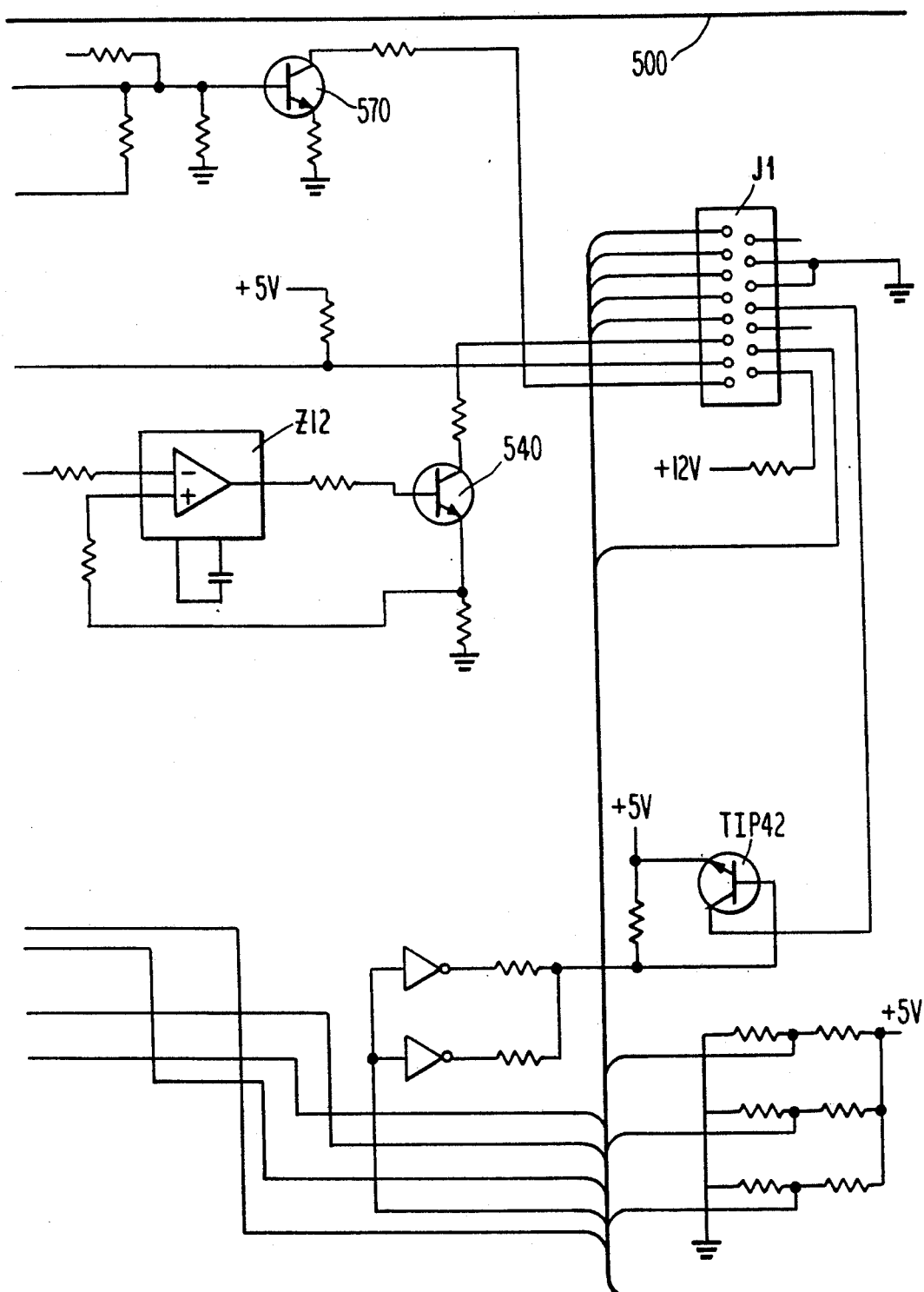
Figure 5D:
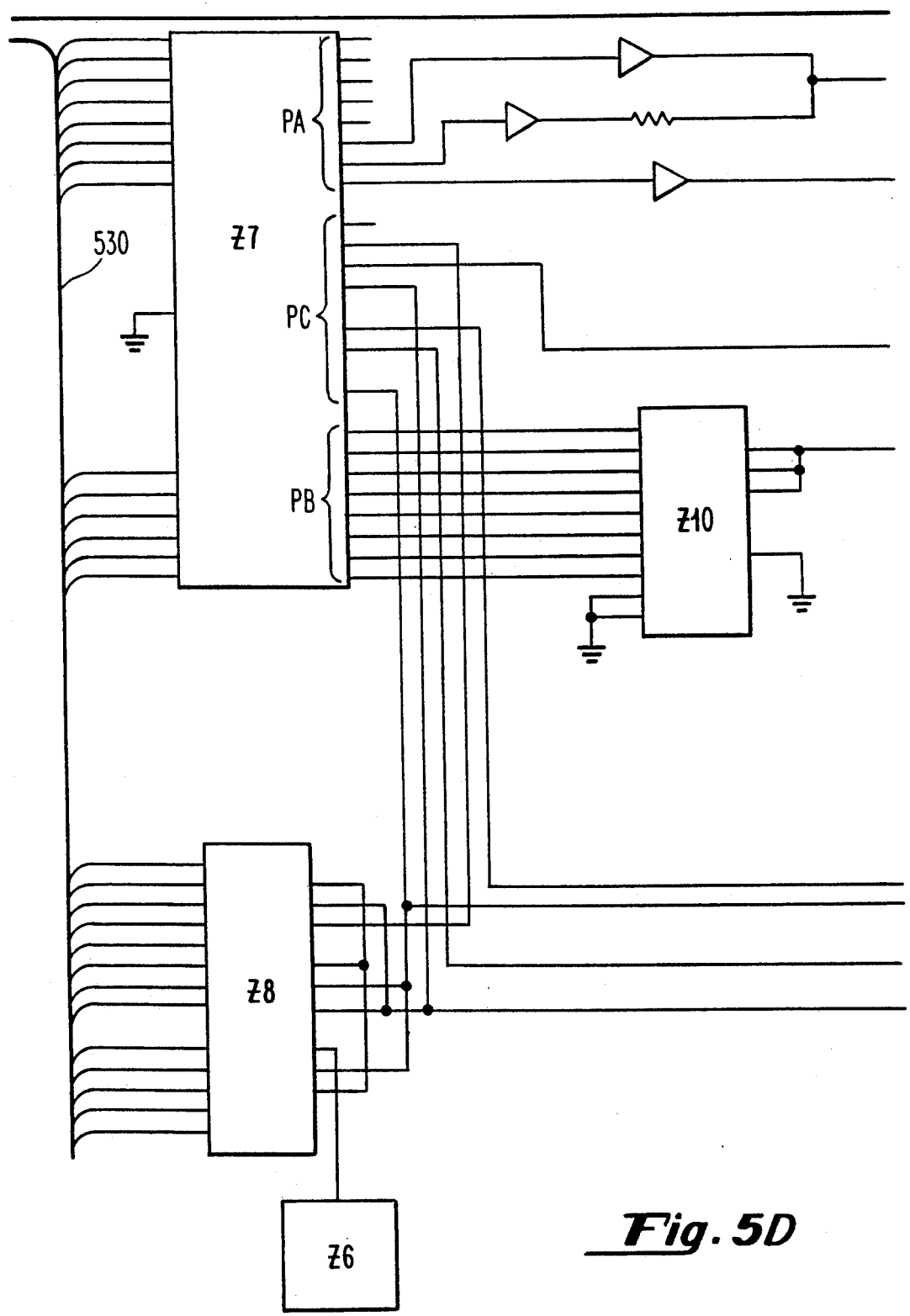
Figure 5E:
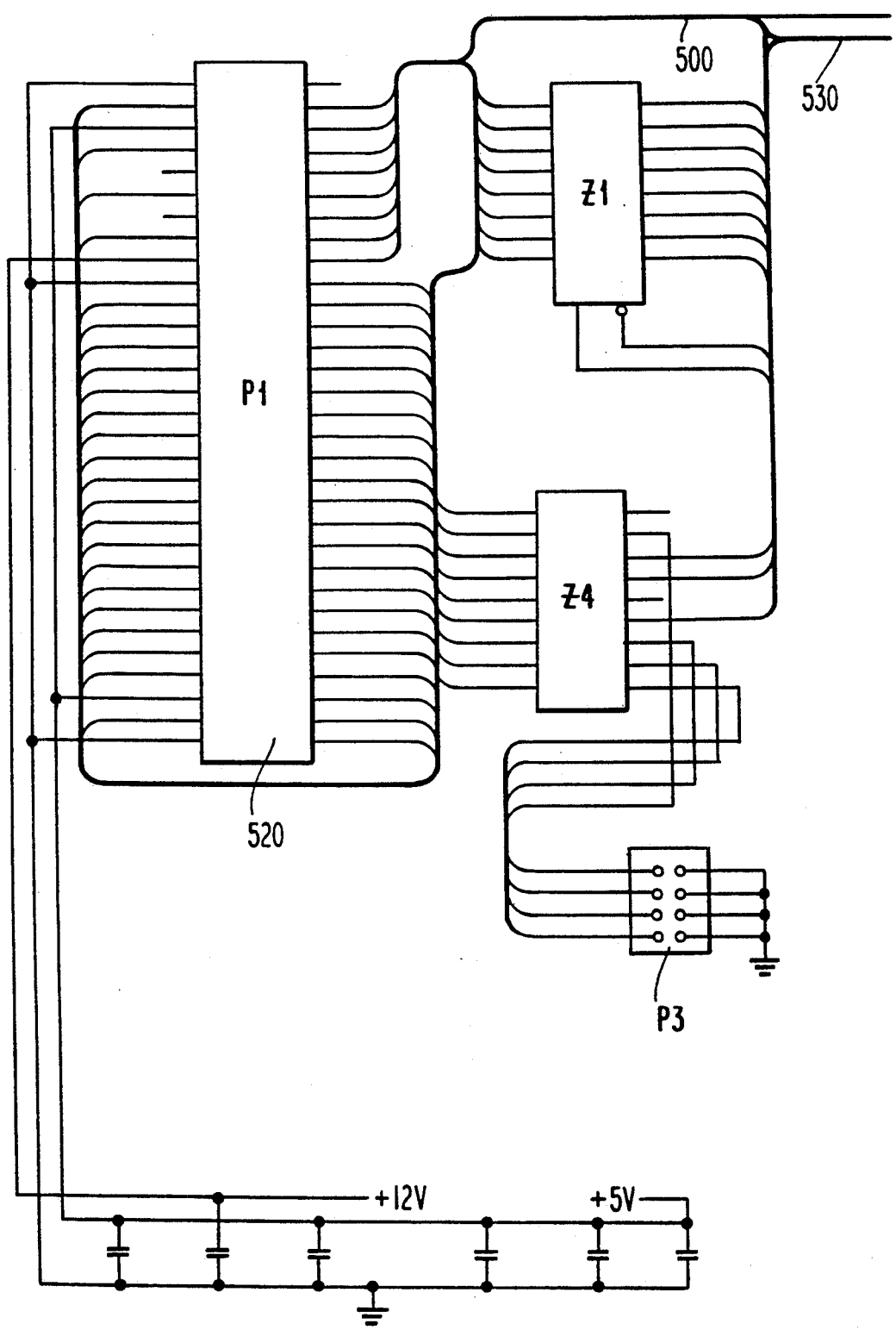

The 5-volt power for the logic on the scanning board in the pupillometer is preferably supplied by the TIP42 transistor (FIG. 5C). Alternatively, an independent power supply in the pupillometer itself may supply power for the logic circuitry on the scanner board. The TIP42 is turned on for the duration of the test through the PC port of Z7 in preferred embodiments.

In further preferred embodiments, data flowing to and from the pupillometer are bussed through the interface PCB and ultimately to the CPU in the computer through connector 520. When data arrives at the computer through connector 520, the CPU in the computer processes the data from the scanning PCB in the pupillometer to provide the desired output data indicative of the pupil's dilation and constriction velocities.

The data indicative of pupil constriction and dilation velocities may be displayed on the computer's CRT screen in a number of ways. For example, a control data set indicative of a normal pupil response from the particular subject under test, or an average normal response derived from a group of subjects under test may be plotted on the screen and compared to the pupil response data extracted during scanning. In this fashion, a comparative indication of the subject's pupil response measured against the subject's normal pupil response, or a control group may be obtained and analyzed to determine impairment.

However, other measures of pupil response may be processed by the CPU and used to evaluate drug or alcohol impairment. For example, the subject's pupil response may be plotted and observed by a trained reader of the pupillometer's output to the computer. Visual analysis of the pupil response by an individual trained to evaluate pupil response as an indication of drug impairment may then be accomplished. Additionally other pupil parameters, and indeed other general parameters unique to the eye, may be obtained and processed by the computer to indicate drug or alcohol impairment with pupillometers provided in accordance with the present invention. Constriction and dilation velocity measurements of the pupil are thus only one way of indicating drug impairment in accordance with the present invention.

Figure 6:
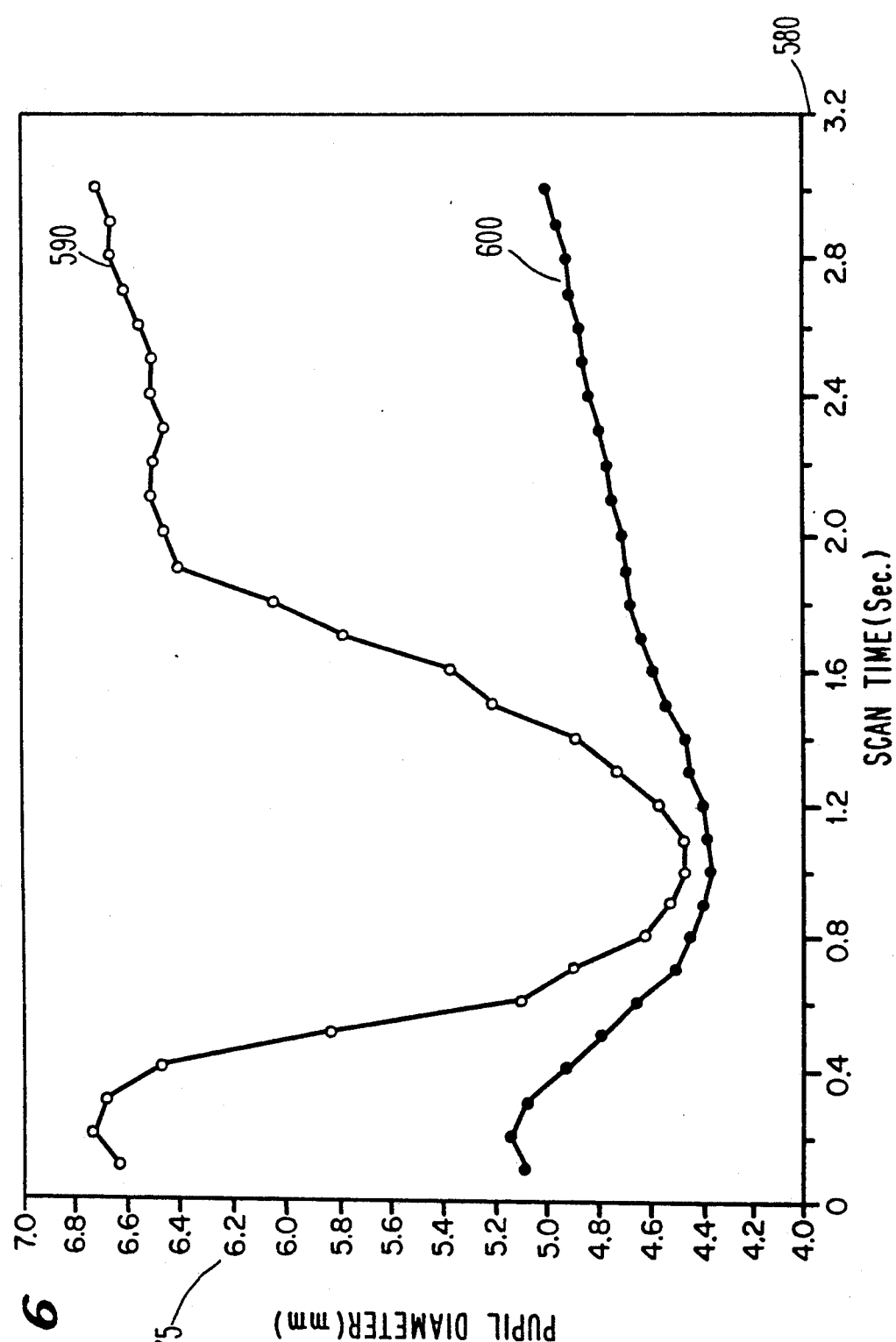
FIG. 6 illustrates a series of graphs of pupil diameter in millimeters versus time of illumination with scanning radiation in seconds which illustrate normal pupil responses to visible light and altered pupil responses, thereby indicating a level of central nervous system impairment.

Referring to FIG. 6, a preferred embodiment of a graph of pupil response provided in accordance with the present invention is shown. As known by those with skill in the art, a standard graphing routine can be implemented on the computer to provide such graphical indications of impairment. In preferred embodiments, the LOTUS 1-2-3 spreadsheet program may be used to provide graphs similar to those shown in FIG. 6. On the Y-axis 575, pupil diameter in millimeters is plotted. On the X-axis 580, the pupil scanning time with infrared radiation provided by the IREDs is plotted in seconds.

Two separate graphs are shown on FIG. 6. The first graph 590 indicates "normal" pupil response which may be the normal pupil response of the subject under test, or the average normal pupil response of a group of individuals who are not impaired. An examination of graph 590 shows that near the zero scan time, the pupil has a maximum dilation. As the pupil is illuminated with light, constriction occurs rather rapidly so that between zero and about one second, minimal pupil size is achieved. The pupil recovers relatively quickly so that by about three seconds, the pupil's maximum redilation level has occurred. As known by those with skill in the art, the derivative of curve 590 at the inflection point at about 0.5 seconds is the maximum pupil constriction velocity, and similarly the derivative of the curve after the minimum point at about 1 second is the pupil redilation velocity.

The second curve plotted in FIG. 6 is shown at 600. This curve is the actual or reduced pupil data scanned from the subject under test and shows impairment. At about zero seconds the subject's pupil size in millimeters is rather low. Furthermore, as indicated by the curve 600 the constriction of the pupil is maximized around one second. However, since the pupil started with a much lower initial diameter, the constriction velocity is much slower which indicates poor response. Additionally after the minimum point of at about one second, the pupil still has not fully recovered by about three seconds, also indicating a much slower redilation velocity and very poor response.

Thus, graph 600 of the pupil response for the subject under test independently indicates impairment, and as compared to graph 590, definitively indicates impairment. The pupillometer provided in accordance with the present invention provides an objective fast, safe, efficient and economical way of indicating drug or alcohol impairment/intoxication based on the pupil constriction and dilation velocities of the subject and does not rely on the subjective judgment of medical professionals. Such results have not heretofore been achieved in the art.

In order to generate graphs illustrated in FIG. 6, pupillometers provided in accordance with the present invention must accurately determine pupil diameters. In preferred embodiments, the pupillometer has the ability to vary the current delivered to the IREDs in the optical block and therefore to vary the intensity of the infrared illumination delivered to the pupil. As discussed earlier, the DAC Z10 on the interface PCB provides the analog level to the IREDs in the optical block as controlled by the output value between 0 and 255 output from the I/O chip Z7. This analog level is driven by transistor 540 which provides the driving current to the IREDs to achieve their desired illumination level.

Achieving the correct illumination level for the IREDs is important for successfully measuring both the pupil diameter and the pupil's dynamic responses such as constriction and dilation velocities. In preferred embodiments, since the OpticRAM is used to sense and record pupil size, it must be illuminated with the correct amount of reflected infrared radiation so that it accurately records pupil size. With too little reflected infrared illumination from the pupil and iris, the OpticRAM will not be able to detect a pupil image. However with too much illumination, the pupil's image may be entirely obliterated by reflection of the infrared radiation from the iris, the cornea, or both.

Figure 7:
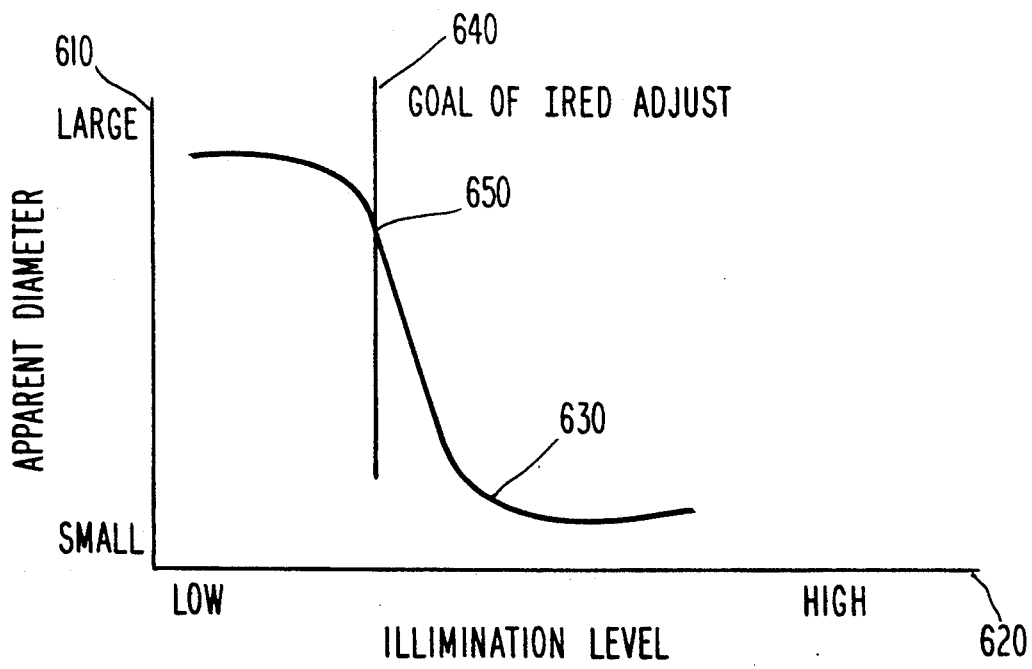
FIG. 7 is a graph of apparent pupil diameter versus illumination level to determine optimal illumination level with scanning infrared radiation.

Referring to FIG. 7, the relationship between the apparent diameter sensed by the OpticRAM and the illumination from the IREDs is illustrated. Apparent diameter is plotted on the Y axis 610. The relative illumination level is plotted on the X axis 620. Generally, an under-illuminated image of the pupil produces an apparent diameter that is greater than the actual diameter of the pupil, and an over-illuminated pupil image produces an apparent diameter that is smaller than the actual pupil size. The relationship between the apparent diameter and the illumination level of the IREDs is illustrated by the graph 630. An optimal illumination level appears as a vertical line 640 which can be considered the goal of an IRED adjust routine given the apparent diameter of the pupil, and the range of illumination levels available to the IREDs. In preferred embodiments, the computer is programmed to bring the illumination level to a point, 650, which achieves a well-lit image without artifacts, and without over-illuminating the pupil and causing a reduction in apparent diameter.

Alternatively, if from previous measurements of a subject a correct IRED level has been determined, a user can pre-select that level and the computer program would skip directly to the measurement cycle after the pupillometer switch 60 is released. Pre-selecting the IRED level in this fashion provides good images on video display 150 immediately after switch 60 is depressed.

In further preferred embodiments, these goals are accomplished in two steps. First, a preliminary adjustment is made while the switch 60 on the pupillometer unit is depressed by the subject under test. Secondly, IRED adjustments are made after the switch is released and before measurements begin to achieve optimal illumination.

Figure 8B:
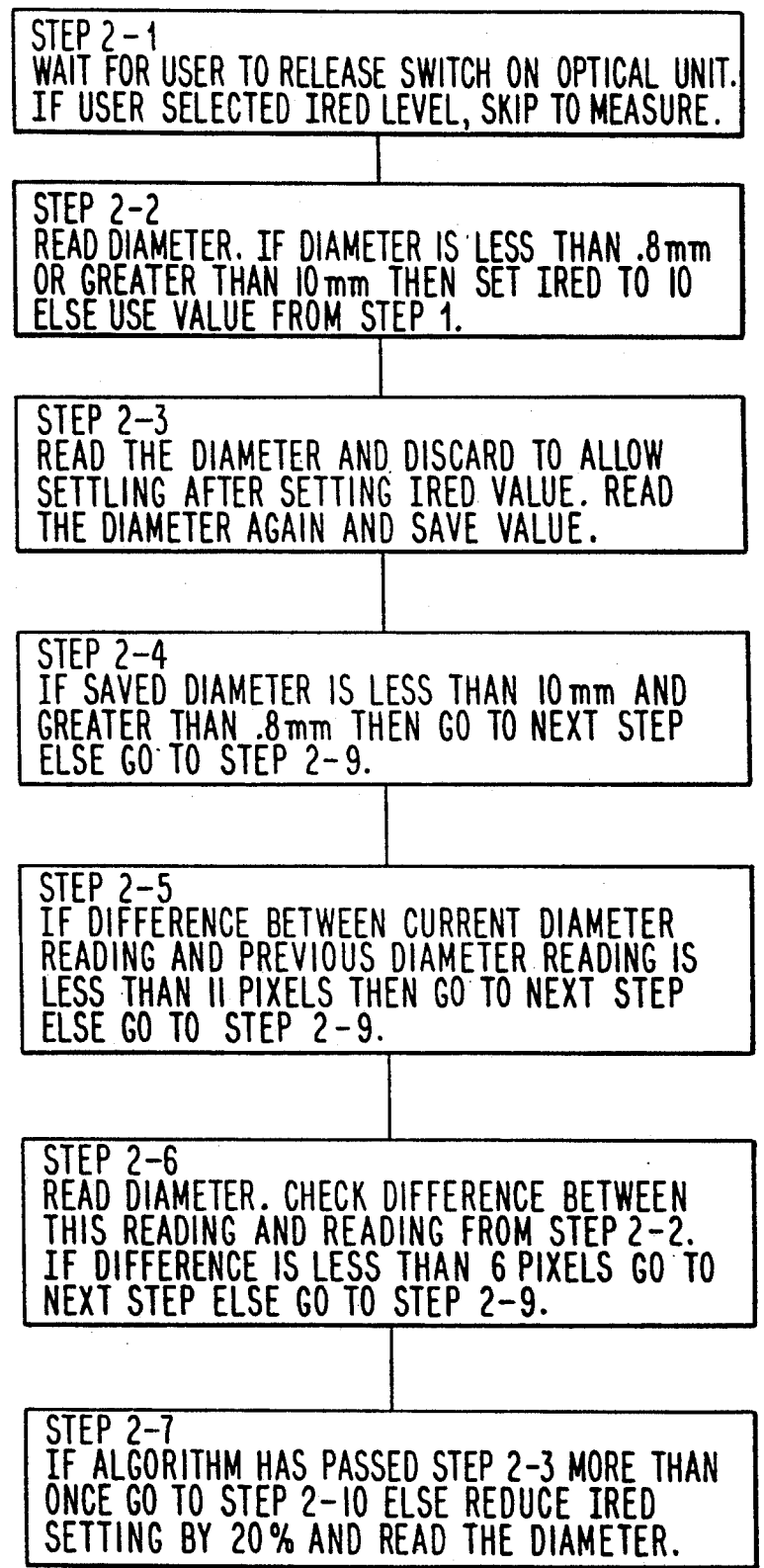

Referring to FIGS. 8A–8C, a flow chart for two steps is illustrated. While the switch on the optical unit is depressed, the first step, indicated by "1-X" where "X" delineates the particular sub-step in the first step routine, begins the IRED adjustment procedure. At step 1-1, the IRED level is set to ten or to a user-selected value. If a user-selected IRED value is input to the pupillometer, the routine immediately goes to step 2-1 (similar notation applies) where final IRED adjustment is accomplished. However, if as in step 1-1 the IRED level is initially set to ten by the I/O chip, then in step 1-2 the OpticRAM takes an initial reading of the pupil diameter and discards that reading to allow the OpticRAM to settle after the initial infrared radiation is set. Then, a second diameter reading is taken and this value is saved by the computer.

At step 1-3, if the second pupil diameter is less than ten millimeters and greater than 0.8 millimeters, then the routine goes to step 1-4. At step 1-4, if the difference between the current diameter reading and the previous diameter reading is less than eleven pixels across the OpticRAM, then the routine goes to step 1-5, otherwise it defaults to step 1-6. If it is the latter, and the IRED setting is greater than two hundred, it is reset to ten, otherwise it is increased by 20% if the apparent diameter of the pupil is greater than three millimeters, or by 10% if the apparent diameter is less than three millimeters and the routine returns to step 1-2. However, if at step 1-4 the routine has not defaulted to step 1-6, then at step 1-5, the IRED level is increased by 20% if the apparent diameter of the pupil is greater than three millimeters or by 10% otherwise.

The pupil diameter is then read, and if the apparent diameter is within eleven pixels of the reading achieved in step 1-2, the routine defaults to step 1-7. Otherwise, step 1-6 is presently accomplished as set forth above, and then step 1-7 is accomplished wherein the CPU in the computer checks for the release of the switch on the pupillometer. If the pupillometer switch is still depressed, then the routine is repeated from 1-2. However, if the subject has released the switch from the pupillometer, then the routine goes on to the second step beginning with step 2-1.

At step 2-1, the computer waits for the user to release the switch on the pupillometer, and at step 2-2 the OpticRAM reads the pupil diameter. If the pupil diameter is less than 0.8 millimeters or greater than ten millimeters and the IRED level is not specified by the user, then the routine sets the IRED level to ten. If the pupil diameter falls between 0.8 and ten millimeters, then the value from sub-step 1 is used.

At step 2-3, the pupil diameter is read again and discarded to allow the OpticRAM to settle after setting an initial IRED value. The pupil diameter is then read and saved by the computer. In step 2-4, the routine determines whether the saved pupil diameter is less than ten millimeters but greater than 0.8 millimeters. If this relationship is not true, then the routine defaults to step 2-9. However, if this relationship is true, then the routine goes on to step 2-5, where it is determined if the difference between the current pupil diameter reading and the previous pupil diameter is less than eleven pixels.

If this relationship does not hold, then the routine again defaults to step 2-9. Otherwise, the routine goes to step 2-6 wherein a third pupil diameter is then read. The difference between the third pupil diameter and the pupil diameter obtained from step 2-2 is determined. If the difference between these two pupil diameters is less than six pixels, then the routine goes on to step 2-7. Otherwise, the routine defaults to step 2-9.

At step 2-7, it is determined whether the routine has passed step 2-3 more than once. If this has occurred, then the routine defaults to step 2-10. Otherwise, the IRED setting is reduced by 20% and a next pupil diameter is read by the OpticRAM. At step 2-8, a comparison between the absolute value of the difference between the most recent step 2-3 pupil diameter reading and the step 2-7 pupil diameter to the absolute value of the difference of the diameter from the most recent step 2-3 diameter and the previous step 2-3 pupil diameter is made. The smallest difference between these two differences is determined, and the IRED value is preferably set to the value which produced the smallest difference.

At this point, the routine defaults to step 2-10. However, if the routine has at any point prior to step 2-8 defaulted to step 2-9, then at step 2-9 it is determined that the IRED setting is greater than two hundred. If this is true, then the IRED value is reset to ten and a counter is set. If the counter is set, then the IRED value is increased by 10%. If the counter is not set, then the IRED value is increased by 20% if the diameter is greater than three millimeters, or by 10% otherwise. At this point, the routine defaults back to step 2-3 until it reaches step 2-8, completes step 2-8, and then defaults to step 2-10.

At step 2-10 it is preferably determined whether the IRED value is greater than 225. If the IRED value is greater than 225, an error message is output to the pupillometer monitor to tell the subject that the current measurement is canceled and to begin again. This error message also tells the pupillometer to start the routine over at step 1-1. However, if the IRED value is less than 225 and no error message is shown to the subject, then at step 2-11 the OpticRAM reads the current apparent diameter of the pupil at the current IRED level.

This diameter is compared to the diameter from the last apparent diameter from step 2-3 and it is then determined if the difference between these two last apparent diameters is greater than six pixels. If this is true, then an error message is shown to the subject and the measurement starts again at step 1-1. Otherwise, at step 2-3 the apparent diameter read is the correct diameter because the difference was less than six pixels and the difference between previous pupil diameters at different IRED levels is less than six pixels. Thus, a correct illumination was achieved and an acceptable apparent diameter was recorded by the OpticRAM.

Setting the IRED is thus accomplished by irradiating the pupil with a first intensity of scanning radiation to obtain a first apparent pupil diameter, and irradiating the pupil with a second intensity of scanning radiation to obtain a second apparent pupil diameter. The first and second apparent pupil diameters are then compared to a control range of pupil diameters to determine which of the first and second apparent pupil diameters fall within the control range and the IRED intensity which produces an apparent pupil diameter that falls within the control range is adopted as the correct setting.

Once the IRED level is set, and the pixels in the OpticRAM have been stimulated by an image, the pupil's diameter must be extracted. In preferred embodiments, pupillometers provided in accordance with the present invention utilize the bilevel, solid state image sensing OpticRAM. The OpticRAM preferably provides a resolution of 256 rows×256 columns which provides efficient diameter extraction. However if greater resolution is desired, higher resolution bilevel, solid state devices or other electro-optic devices could be used.

Figure 9:
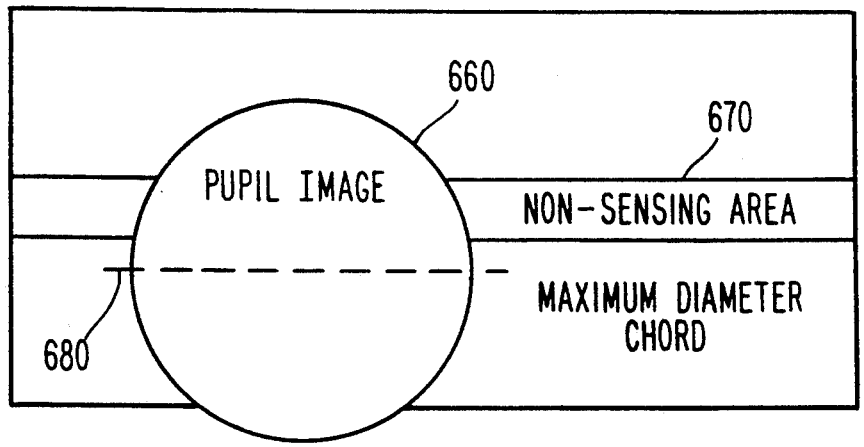
FIG. 9 is a schematic representation of a sensing element used to monitor the pupil and to extract the pupil's diameter from reflected scanning radiation.

The diameter is extracted by the computer according to a preferred diameter extraction routine. In preferred embodiments, the diameter is calculated by finding the maximum length chord across the pupil image on the OpticRAM which is approximately circular. Referring to FIG. 9, the face of the OpticRAM is illustrated. The approximately circular pupil image is shown at 660. The OpticRAM is bisected down the center by a non-sensing area 670 which provides a reference line on the sensor according to which the pupil diameter can be measured.

The maximum diameter chord across the circular pupil image is shown at 680. In preferred embodiments, the chord length is calculated by scanning a row from the top of the sensor image until two bytes of 0×FF are found, thereby indicating sixteen consecutive dark pixels in a row. In further preferred embodiments, the row is then scanned from the bottom of the sensor until a similar two bytes, 0×FF, are found. The difference between these two points will be the maximum chord length.

As described above, pupil diameter extraction relies on the physical layout of OpticRAM image sensor. The sensor area consists of two rectangular areas separated by the non-sensing area 670 in between. In further preferred embodiments, the non-sensing area 670 is positioned at the center of the image when the pupil is properly aligned on the sensor. The diameter extraction routine then begins by assuming a properly aligned image and checks the chord lengths on either side of the non-sensing area 670 first.

Figure 10:
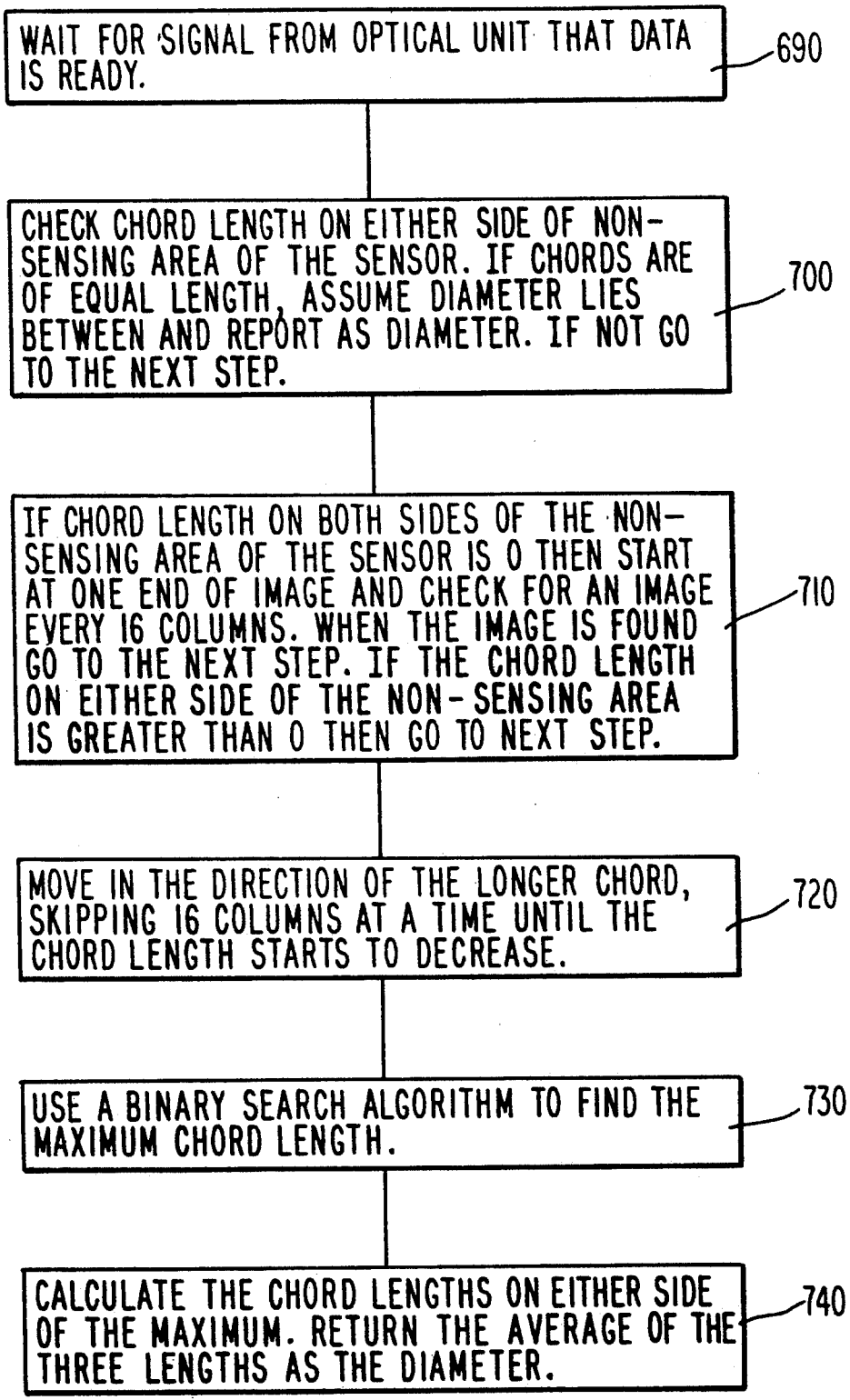
FIG. 10 is a flow chart of a preferred method for extracting the pupil's diameter from the sensing element shown in FIG. 9.

A preferred embodiment of the diameter extraction routine is illustrated by the flowchart of FIG. 10. At step 690, a signal is received from the optical block that indicates that diameter extraction can begin. At step 700, the chord length on either side of non-sensing area 670 is checked. If the chords are of equal length, then it is assumed that the diameter lies between the two points, and the difference between these two points is a chord length of maximum diameter, that is, the pupil size. If however, the chords are not of equal length, then the routine goes on to step 710.

At step 710, it is determined whether the chord lengths on both sides of the non-sensing area 670 are zero. If this is true, then scanning occurs every sixteen columns to find the image beginning at one end of the OpticRAM. When the image is found, the routine goes on to step 720. However, if the chord lengths on either side of the non-sensing area are greater than zero, then the routine immediately defaults to step 720.

At step 720, scanning occurs in the direction of the longer chord, skipping sixteen columns at a time until the chord length begins to decrease. Then, at step 730, preferably a binary search is accomplished to find the maximum chord length. While a binary search has been discovered to be efficient to determine maximum chord length, it will be recognized by those with skill in the art that other types of searches to find the maximum chord length could be utilized. The routine then moves on to step 740 where the chord lengths on either side of the maximum length chord are calculated and the pupil diameter is determined by taking an average of these three chord lengths and calling this the diameter of the pupil. This value is then used to determine impairment.

It will be recognized by those with skill in the art that other types of sensors could be used to obtain pupil diameters and pupil responses. While the 64K OptiCRAM has been found effective and economical, other types of sensors could be used to achieve pupil monitoring. As mentioned previously, CCDs, SLMs, and other electro-optic devices could all be adapted to provide pupil responses. With these other devices, other diameter extraction routines could be devised and implemented to satisfy the pupil diameter extraction function described above.

Pupillometers provided in accordance with the present invention thus perform accurate, effective and economical pupillometry on subjects. With pupillometers provided in accordance with the present invention, accurate drug and alcohol impairment testing can be repeatedly accomplished and will provide accurate data concerning an individual's ability to perform his or her various life tasks. Furthermore, the pupillometers described and claimed herein can be used in research and diagnostic settings wherein pupil response is an indication of various physiological aspects of a subject's central nervous system. Pupillometers provided in accordance with the present invention are generally useful for all such applications.

There have thus been described certain preferred embodiments of methods and apparatus for determining pupil response, and pupillometers for research, diagnostic, and drug and alcohol impairment testing. While preferred embodiments have been described and disclosed, it will be recognized by those with skill in the art that modifications are within the true spirit and scope of the invention. The following claims are intended to cover all such modifications.

What is claimed is:

1. A portable, scanning, self-measuring pupillometer comprising:
    eye orbit housing means for positioning at least one eye orbit for scanning by the pupillometer;
    radiating means interfaced with the housing means for irradiating at least one eye with scanning radiation;
    sensing means adapted to receive reflected radiation from the eye irradiated by the radiating means, the sensing means being further adapted to respond to a contrast between radiation reflected from the iris of the eye and radiation reflected from the pupil of the eye; and
    centering means interfaced with the sensing means for presenting to a subject an image of the pupil on the sensing means as the subject is using the pupillometer, so that the subject can center the image of the pupil on the sensing means.

2. The pupillometer recited in claim 1 further comprising scanning means interfaced with the sensing means for controlling pupillometer scanning of the eye.

3. The pupillometer recited in claim 2 further comprising a plurality of optical elements for directing the scanning radiation to the eye and the reflected radiation from the eye to the sensing means.

4. The pupillometer recited in claim 3 further comprising stimulus means interfaced with the eye orbit housing means for irradiating the eye with light to cause pupil constriction.

5. The pupillometer recited in claim 4 wherein the scanning radiation is infrared radiation.

6. The pupillometer recited in claim 5 wherein the radiating means is at least one infrared emitting diode.

7. The pupillometer recited in claim 6 wherein the stimulus means is at least one light emitting diode which radiates visible light.

8. The pupillometer recited in claim 7 wherein the centering means comprises a video monitor.

9. The pupillometer recited in claim 1 further comprising interface means operatively coupled to the scanning means for interfacing data gathered by the sensing means to an outside environment.

10. The pupillometer recited in claim 9 further comprising processing means operatively coupled to the interface means for reducing the data gathered by the sensing means and controlling the scanning means.

11. The pupillometer recited in claim 10 further comprising a cathode ray tube monitor interfaced with the processing means for displaying the data reduced by the processing means to indicate a pupil parameter.

12. A system for measuring pupil size comprising:
    a portable scanning pupillometer further comprising;
    eye orbit housing means for interfacing at least one eye of a subject to the pupillometer for scanning;
    electromagnetic radiating means interfaced with the eye orbit housing means for irradiating at least one of the eyes in the eye orbits with radiation;
    a sensing element positioned to intercept reflected radiation from the eye as it is illuminated by the radiating means, the sensing element being adapted to distinguish a contrast between the iris and the pupil of the eye as irradiated by the electromagnetic radiating means;
    centering means interfaced with the sensing element for presenting to a subject an image of the pupil on the sensing element while the subject is using the pupillometer, so that the subject can center the image of the pupil on the sensing element;
    junction interface means interfaced with the centering means for interfacing the contrast signal with an outside environment; and
    processing means interfaced through the junction interface means to the sensing element for processing signals corresponding to the contrast difference between the iris and the pupil.

13. The system recited in claim 12 further comprising scanning means interfaced with the sensing element and the junction interface means for controlling pupillometer scanning of the eye with the radiation.

14. The system recited in claim 13 further comprising a plurality of optical elements for directing the radiation from the eye to the sensing element.

15. The system recited in claim 14 further comprising excitor means interfaced with the sensing element for irradiating the eye with visible light to cause pupil constriction.

16. The system recited in claim 15 wherein the electromagnetic radiating means radiates infrared radiation.

17. The system recited in claim 16 wherein the electromagnetic radiating means is at least one infrared-emitting diode.

18. The system recited in claim 17 further comprising stimulus means interfaced with the eye orbit housing means for irradiating the eye with light to cause pupil constriction.

19. The system recited in claim 18 wherein the stimulus means is at least one light-emitting diode which radiates visible light.

20. The system recited in claim 19 wherein the centering means comprises a cathode ray tube.

21. The system recited in claim 20 wherein the processing means comprises:

a computer adapted to process contrast data gathered by the sensing element;

a printed circuit board which modifies the computer and interfaces the scanning means to the computer; and display means interfaced with the printed circuit interface board for displaying the processed contrast data that has been reduced by the computer.

22. The system recited in claim 18 wherein the display means is a cathode ray tube video monitor.

23. The system recited in claim 22 wherein the processed contrast data displayed on the cathode ray tube video monitor is constriction and dilation velocities of the pupil when irradiated with visible light by the excitor means.

* * * * *